United States Patent
Konh et al.

(10) Patent No.: US 11,911,111 B2
(45) Date of Patent: Feb. 27, 2024

(54) AUTONOMOUS SYSTEM AND METHOD FOR PLANNING, TRACKING, AND CONTROLLING THE OPERATION OF STEERABLE SURGICAL DEVICES

(71) Applicant: UNIVERSITY OF HAWAII, Honolulu, HI (US)

(72) Inventors: Bardia Konh, Honolulu, HI (US); Omid Haji Maghsoudi, Philadelphia, PA (US)

(73) Assignee: University of Hawaii, Honolulu, HI (US)

( * ) Notice: Subject to any disclaimer, the term of this patent is extended or adjusted under 35 U.S.C. 154(b) by 978 days.

(21) Appl. No.: 16/551,001

(22) Filed: Aug. 26, 2019

(65) Prior Publication Data
US 2020/0060772 A1    Feb. 27, 2020

Related U.S. Application Data

(60) Provisional application No. 62/722,543, filed on Aug. 24, 2018.

(51) Int. Cl.
*A61B 17/00* (2006.01)
*A61B 34/20* (2016.01)
(Continued)

(52) U.S. Cl.
CPC .......... *A61B 34/20* (2016.02); *A61B 17/3478* (2013.01); *A61B 34/32* (2016.02);
(Continued)

(58) Field of Classification Search
CPC ................ A61B 17/3478; A61B 34/32; A61B 2017/00314; A61B 2017/00323;
(Continued)

(56) References Cited

U.S. PATENT DOCUMENTS 5,668,998 A    9/1997  Mason et al.
2011/0112549 A1*  5/2011  Neubach ................ A61B 34/20
                                                              606/130
(Continued)

FOREIGN PATENT DOCUMENTS

WO    2018183832 A1    10/2018

OTHER PUBLICATIONS

Haga et al, Active Bending Catheter and Endoscope Using Shape Memory Alloy Actuators, Oct. 18, 2010, Intech Open, Shape Memory Alloys, pp. 107-126 (Year: 2010).*

(Continued)

*Primary Examiner* — Rochelle D Turchen
(74) *Attorney, Agent, or Firm* — Withrow & Terranova, P.L.L.C.; Vincent K. Gustafson

(57) ABSTRACT

An autonomous system and method for controlling the operation of a steerable surgical device includes multiple surgical device actuation elements, an imaging apparatus (e.g., ultrasound) arranged external to a mammalian body, and at least one processor. The processor(s) is/are configured to generate a transit path between an insertion point and a target point, control the surgical device actuation elements to advance the steerable surgical device along one or more segments of the transit path, identify deviation of position relative to the transit path utilizing signals from the imaging apparatus and generate an updated transit path, and control the surgical device actuation elements to advance the steerable surgical device along at least one segment of the updated transit path. Transit of the steerable surgical device between the insertion point and the target point may be controlled without human intervention.

15 Claims, 19 Drawing Sheets

(51) Int. Cl.
  *A61B 34/32* (2016.01)
  *A61B 17/34* (2006.01)
  *G06N 5/01* (2023.01)
  *A61B 34/30* (2016.01)
  *A61B 34/10* (2016.01)
(52) U.S. Cl.
  CPC ...... *G06N 5/01* (2023.01); *A61B 2017/00314* (2013.01); *A61B 2017/00323* (2013.01); *A61B 2017/00367* (2013.01); *A61B 2017/00867* (2013.01); *A61B 2034/107* (2016.02); *A61B 2034/2063* (2016.02); *A61B 2034/2065* (2016.02); *A61B 2034/301* (2016.02)
(58) Field of Classification Search
  CPC .... A61B 2017/00867; A61B 2034/107; A61B 2034/2063; A61B 2034/301
  See application file for complete search history.

(56) References Cited

U.S. PATENT DOCUMENTS

| | | | | |
|---|---|---|---|---|
| 2013/0296885 | A1* | 11/2013 | Desai | A61B 17/3417 606/130 |
| 2013/0345718 | A1* | 12/2013 | Crawford | A61B 90/39 606/130 |
| 2014/0276586 | A1* | 9/2014 | Swaney | A61B 17/3417 604/95.01 |
| 2018/0085926 | A1* | 3/2018 | Kogan | B25J 9/1682 |
| 2019/0223962 | A1* | 7/2019 | Roldan | A61B 34/10 |
| 2019/0374746 | A1 | 12/2019 | Konh | |

OTHER PUBLICATIONS

Achanta, R et al., "SLIC Superpixels," EPFL Technical Report 149300, Jun. 2010, 15 pages.
Author Unknown, "pydicom/pynetdicom: A Python implementation of the DICOM networking protocol," retrieved Feb. 3, 2020 from https://github.com/pydicom/pynetdicom3, GitHub, Inc., 5 pages.
Author Unknown, "pydicom/pynetdicom: Read, modify and write DICOM files with python code," retrieved Feb. 3, 2020 from https://github.com/pydicom/pydicom GitHub, Inc., 5 pages.
Abolhassani, N. et al., "Needle insertion into soft tissue: A survey," Medical Engineering & Physics, vol. 29, Issue 4, 2007, Elsevier Ltd., pp. 413-431.
Ayvali, E., "Optical Flow-Based Tracking of Needles and Needle-Tip LocalizationUsing Circular Hough Transform in Ultrasound Images," Annals of Biomedical Engineering, vol. 43, No. 8, Aug. 2015, pp. 1828-1840.
Ayvali, E. et al., "Towards a discretely actuated steerable cannula for diagnostic and therapeutic procedures," The International Journal of Robotics Research, vol. 31, Issue 5, Apr. 2012, Sage, pp. 588-603.
Black, R.J et al., "Characterization of optically actuated MRI-compatible active needles for medical interventions," Apr. 15, 2014, Behavior and Mechanics of Multifunctional Materials and Composites, Proc. of SPIE, vol. 9058, SPIE, 8 pages.
Chatelain, P. et al., "Real-time needle detection and tracking using a visually servoed 3D ultrasound probe," 2013 IEEE International Conference on Robotics and Automation (ICRA), May 6-10, 2013, Karlsruhe, Germany, IEEE, pp. 1676-1681.
Datla, N.V. et al., "A model to predict deflection of bevel-tipped active needle advancing in soft tissue," Medical Engineering & Physics, vol. 36, No. 3, Mar. 2014, available online Dec. 2013, Elsevier Ltd., pp. 285-293.
Datla, N.V. et al., "Flexure-Based Active Needle for Enhanced Steering Within Soft Tissue," Journal of Medical Devices, vol. 9, Dec. 2015, ASME, 6 pages.
Datla, N.V. et al., "Polyacrylamide phantom for self-actuating needle-tissue interaction studies," Medical Engineering & Physics, vol. 36, No. 1, Jan. 2014, available online Aug. 2013, Elsevier Ltd., pp. 140-145.
Datla, N.V. et al., "Studies with SMA Actuated Needle for Steering Within Tissue," SMASIS2014-7523, Proceedings of the ASME 2014 Smart Materials, Adaptive Structures and Intelligent Systems, Sep. 8-10, 2014, Newport, Rhode Island, USA, ASME, 4 pages.
De Jong, T.L. et al., "Needle deflection in thermal ablation procedures of liver tumors: a CT image analysis," Medical Imaging 2018: Image-Guided Procedures, Robotic Interventions, and Modeling, Proceedings of SPIE, vol. 10576, Mar. 2018, SPIE, 6 pages.
Duindam, V. et al., "Screw-Based Motion Planning for Bevel-Tip Flexible Needles in 3D Environments with Obstacles," 2008 IEEE International Conference on Robotics and Automation (ICRA), May 19-23, 2008, Pasadena, CA, IEEE, pp. 2483-2488.
Elgezua, Inko, et al., "Survey on Current State-of-the-Art in Needle Insertion Robots: Open Challenges for Application in Real Surgery," The First CIRP Conference on Biomanufacturing, 2014, Elsevier B.V., pp. 94-99.
Frasson, L. et al., "Experimental evaluation of a novel steerable probe with a programmable bevel tip inspired by nature," Journal of Robotic Surgery, vol. 6, 2012, published online Jun. 2011, Springer, pp. 189-197.
Gerboni, G. et al., "Highly Articulated Robotic Needle Achieves Distributed Ablation of Liver Tissue," IEEE Robotics and Automation Letters, vol. 2, Issue 3, 2017, IEEE, 8 pages.
Hasegawa, T. et al., "A control system to compensate the hysteresis by Preisach Model on SMA actuator," 1998 International Symposium on Micromechatronics and Human Science, Nov. 25-28, 1998, Nagoya, Japan, IEEE, pp. 171-176.
Karaman, S. et al., "Incremental Sampling-based Algorithms for Optimal Motion Planning," Robotics: Science and Systems VI Online Proceedings, Jun. 27-30, 2010, Zaragoza, Spain, available at http://www.roboticsproceedings.org/rss06/index.html, 8 pages.
Karaman, S. et al., "Sampling-based Algorithms for Optimal Motion Planning," International Journal of Robotics Research, vol. 30, Issue 7, Special Issue on Robotics: Science and Systems 2010, Jun. 2011, Sage Journals, pp. 846-894.
Karimi, S. et al., "SMA Wire Characterization for 3D Steerable Active Devices," DMD2018-6856, Proceedings of the 2018 Design of Medical Devices Conference, DMD2018, Apr. 9-12, 2018, Minneapolis, MN, USA, ASME, 3 pages.
Karimi, S. et al., "Towards the development of a triple SMA actuated vertical tube," Active and Passive Smart Structures and Integrated Systems XII, Proceedings of SPIE, vol. 10595, Mar. 2018, SPIE, 5 pages.
Khadem, M. et al., "Semi-Automated Needle Steering in Biological Tissue Using an Ultrasound-Based Deflection Predictor," Annals of Biomedical Engineering, vol. 45, No. 4, Apr. 2017, available online Sep. 2016, Biomedical Engineering Society, pp. 924-938.
Konh, B. et al., "A portable integrated system to control an active needle," Industrial and Commercial Applications of Smart Structures Technologies, Proceedings of SPIE, vol. 10166, Apr. 2017, SPIE, 6 pages.
Konh, B. et al., "Application of SMA Wire for an Active Steerable Cannula," SMASIS2013-3142, Proceedings of the ASME 2013 Conference on Smart Materials, Adaptive Structures and Intelligent Systems, SMASIS2013, Sep. 16-18, 2013, Snowbird, Utah, USA, ASME, 5 pages.
Konh, B. et al., "Design and Fabrication of a Robust Active Needle using SMA Wires," DMD2017-3470, Proceedings of the 2017 Design of Medical Devices Conference, DMD2017, Apr. 10-13, 2017, Minneapolis, Minnesota, USA, ASME, 2 pages.
Konh, B. et al., "Design, Development, and Evaluation of a Two Way Actuated Steerable Needle," SMASIS2015-9084, Proceedings of the ASME 2015 Conference on Smart Materials, Adaptive Structures and Intelligent Systems, SMASIS2015, Sep. 21-23, 2015, Colorado Springs, Colorado, USA, ASME, 5 pages.
Konh, B. et al., "Design optimization study of a shape memory alloy active needle for biomedical applications," Medical Engineering and Physics, vol. 37, Issue 5, May 2015, Elsevier Ltd., pp. 469-477.
Konh, B. et al., "Evaluating the performance of an advanced smart needle prototype inside tissue," Active and Passive Smart Structures and Integrated Systems 2017, Proceedings of SPIE, vol. 10164, Apr. 2017, SPIE, 5 pages.

(56) References Cited

OTHER PUBLICATIONS

Konh, B. et al., "Feasability of Shape Memory Alloy Wire Actuation for an Active Steerable Cannula," Journal of Medical Devices, vol. 9, Jun. 2015, ASME, 11 pages.

Konh, B. et al., "Feasability study of an active soft catheter actuated by SMA wires," Smart Structures and NDE for Industry 4.0, Proceedings of SPIE, vol. 10602, Mar. 2018, SPIE, 5 pages.

Konh, B. et al., "Finite Element Simulation of an Active Surgical Needle for Prostrate Brachytherapy," FMD2013-16049, Proceedings of the ASME/FDA 2013 1st Annual Frontiers in Medical Devices: Applications of Computer Modeling and Simulation, FMD2013, Sep. 11-13, 2013, Washington, DC, USA, ASME, 2 pages.

Konh, B. et al., "Simulation and experimental studies in needle-tissue interactions," Journal of Clinical Monitoring and Computing, vol. 31, No. 4, 2017, published online Jul. 18, 2016, Springer Science+Business Media Dordrecht, pp. 861-872.

Konh, B., "Smart Surgical Needle Actuated by Shape Memory Alloys for Percuteneous Procedures," A Dissertation submitted to the Temple University Graduate Board in partial fulfillment of the requirements for the Degree of Doctor of Philosophy, May 2016, 143 pages.

Krempien, R. et al., "Frameless Image Guidance Improves Accuracy in Three-Dimensional Interstitial Brachytherapy Needle Placement," International Journal of Radiation Onoclogy Biology Physics, vol. 60, Issue 5, Dec. 2004, Elsevier, pp. 1645-1651.

Madhsoudi, O. et al., "Application of Superpixels to Segment Several Landmarks in Running Rodents," Pattern Recognition and Image Analysis, vol. 28, No. 3, Apr. 2018, Pleiades Publishing, Ltd., pp. 468-482.

Maghsoudi, Omid, et al., "Superpixels Based Marker Tracking Vs. Hue Thresholding In Rodent Biomechanics Application," 51st Asilomar Conference on Signals, Systems, and Computers, Oct. 2017, arXiv:1710.06473v4 [cs.CV], May 28, 2018, 6 pages.

Maghsoudi, Omid, et al., "Three-dimensional based landmark tracker employing a superpixels method for neuroscience, biomechanics, and biology studies," International Journal of Imaging Systems and Technology, Mar. 2019, Wiley Periodicals, Inc., 12 pages.

Majewicz, A. et al., "Behavior of Tip-Steerable Needles in Ex Vivo and In Vivo Tissue," IEEE Transactionson Biomedical Engineering, vol. 59, No. 10, Oct. 2012, available online Jun. 2012, IEEE, pp. 2705-2715.

Misra, S. et al., "Mechanics of Flexible Needles Robotically Steered through Soft Tissue," The International Journal of Robotics Research, vol. 29, No. 13, Sage, pp. 1640-1660.

Najafi, M. et al., "Single camera closed-form real-time needle trajectory tracking for ultrasound," Medical Imaging 2011: Visualization, Image-Guided Procedures, and Modeling, Proceedings of SPIE, vol. 7964, Mar. 1, 2011, 7 pages.

Podder, T. et al., "A novel curvilinear approach for prostate seed implantation," Medical Physics, vol. 39, No. 1, Apr. 2012, American Association of Physicists in Medicine, pp. 1887-1892.

Podder, T. et al., "In vivo motion and force measurement of surgical needle intervention during prostate prachytherapy," Medical Physics, vol. 33, No. 8, Aug. 2006, American Association of Physicists in Medicine, pp. 2915-2922.

Reed, K. et al., "Modeling and Control of Needles With Torsional Friction," IEEE Transactions on Biomedical Engineering, vol. 56, No. 12, Dec. 2009, IEEE, pp. 2905-2916.

Roesthuis, R. et al., "Mechanics-Based Model for Predicting In-Plane Needle Deflection with Multiple Bends," The Fourth IEEE RAS/EMBS International Conference on Biomedical Robotics and Biomechatronics, Jun. 24-27, 2012, Roma, Italy, IEEE, pp. 69-74.

Romano, J. et al., "Teleoperation of Steerable Needles," 2007 IEEE International Conference on Robotics and Automation, Apr. 10-14, 2007, Roma, Italy, IEEE, pp. 934-939.

Ryu, S.K. et al., "Feasibility Study of an Optically Actuated MR-compatible Active Needle," 2011 IEEE/RSJ International Conference on Intelligent Robots and Systems, Sep. 25-30, 2011, San Francisco, CA, USA, IEEE, pp. 2564-2569.

Ryu, S.K. "Optically Controlled Magnetic Resonance Imaging Compatible Needle," Dissertation submitted to the Department of Mechanical Engineering and the Committee on Graduate Studies of Standford University, Dec. 2012, available at <http://purl.stanford.edu/ht443cf9111>, 127 pages.

Sakai, A., "PythonRobotics: Python sample codes for robotics algorithms," retrieved Feb. 2, 2020 from https://github.com/AtsushiSakai/PythonRobotics, GitHib, Inc., 26 pages.

Scali, M. et al., "Needle-like instruments for steering through solid organs: A review of the scientific and patent literature," Proceedings of the Institution of Mechanical Engineers Part H, Journal of Engineering in Medicine, vol. 231, No. 3, Dec. 2016, IMechE, pp. 250-265.

Song, G. et al., "Precision tracking control of shape memory alloy actuators using neural networks and a sliding-mode based robust controller," Smart Materials and Structures, vol. 12, No. 2, Mar. 27, 2003, Institute of Physics Publishing, pp. 223-231.

Su, H. et al., "A MRI-Guided Concentric Tube Continuum Robot with Piezoelectric Actuation: A Feasibility Study," 2012 IEEE International Conference on Robotics and Automation, May 14-18, 2012, Saint Paul, Minnesota, USA, IEEE, pp. 1939-1945.

Swaney, P. et al., "A Flexure-Based Steerable Needle: High Curvature With Reduced Tissue Damage," IEEE Transactions on Biomedical Engineering, vol. 60, No. 4, Apr. 2013, available online Nov. 2012, IEEE, pp. 906-909.

Swensen, J. et al., "Torsional Dynamics of Steerable Needles: Modeling and Fluoroscopic Guidance," IEEE Transactions on Biomedical Engineering, vol. 61, No. 11, Nov. 2014, IEEE, pp. 2707-2717.

Van De Berg, N. et al., "Design Choices in Needle Steering—A Review," IEEE/ASME Transactions on Mechatronics, vol. 20, No. 5, Oct. 2015, IEEE, pp. 2172-2183.

Xia, W. et al., "Looking beyond the imaging plane: 3D needle tracking with a linear array ultrasound probe," Scientific Reports, vol. 7, Article No. 3674, published online Jun. 16, 2017, 9 pages.

Zhao, Y. et al., "Biopsy Needle Localization and Tracking Using ROI-RK Method," Abstract and Applied Analysis, vol. 2014, Article ID 973147, Hindawi Publishing Corporation, 7 pages.

\* cited by examiner

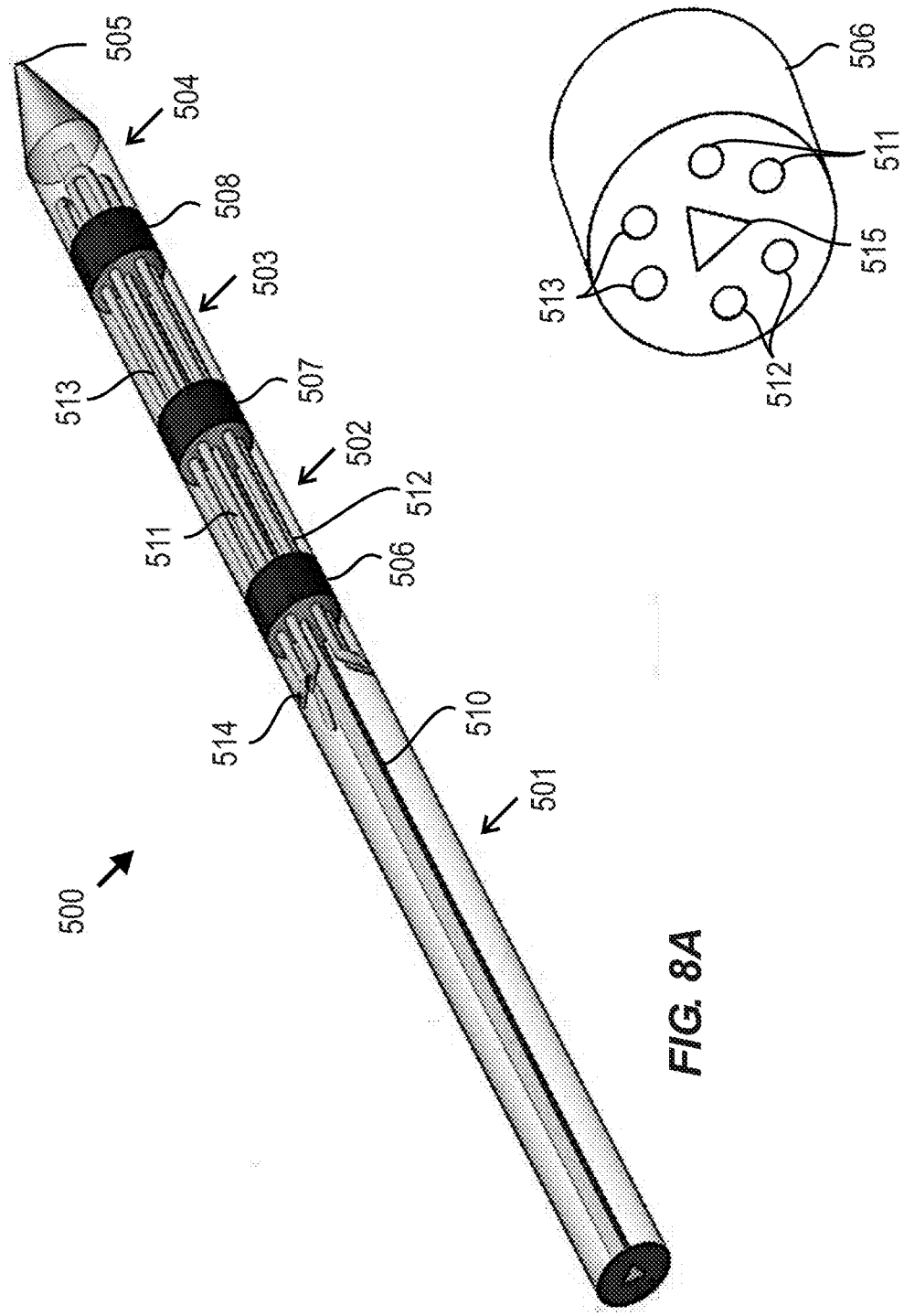

AUTONOMOUS SYSTEM AND METHOD FOR PLANNING, TRACKING, AND CONTROLLING THE OPERATION OF STEERABLE SURGICAL DEVICES

STATEMENT OF RELATED APPLICATION(S)

This application claims benefit of U.S. Provisional Patent Application No. 62/722,543 filed on Aug. 24, 2018, wherein the entire contents of the foregoing application are hereby incorporated by reference herein.

TECHNICAL FIELD

This invention relates to systems and methods for controlling operation of steerable surgical devices that are insertable in tissues of mammalian bodies.

BACKGROUND

Surgical needles are commonly used in percutaneous diagnostic and therapeutic procedures. These procedures include tissue sample removal (biopsy), internal radiotherapy (brachytherapy), thermal ablations, and targeted drug delivery. The success of these procedures highly depends on the accuracy of needle placement at target locations. For example, incorrect positioning of the biopsy needle could result in a false diagnosis. Similarly, in brachytherapy, inaccurate positioning of the radioactive seeds could cause damage to the healthy tissue instead of attacking the cancerous cells. Precise delivery of therapeutic drugs to the diseased tissue or taking biopsy samples from suspicious tissue for diagnosis procedures is the most important factor governing the success of needle-based procedure. Conventionally, rigid passive needles (e.g., 17 or 18 gauge needles with 2.4 mm outer diameter and 1.8 mm inner diameter, suitable for passing radioactive seeds typically about 0.8 mm in diameter) are used in a straight path to reach the target. These needles would leave limited room for adjustment after their insertion into the patient's body. However, unpredicted factors such as human error, tissue deformation, and nonlinear and nonhomogeneous properties of the tissue undermines the placement accuracy.

As an alternative to rigid passive needles, flexible steerable needles have been proposed for enhanced navigation inside patient tissues. Passive bevel-tip needles beneficially utilize unbalanced forces on their tip to create a curved path inside the tissue and reach the target. This curved path could be used to maneuver around sensitive organs during surgical intervention. However, trajectory planning with passive needles is complicated and sometimes inaccurate. With passive needles, the deflection is basically governed by needle-tissue interactions. Passive needles with a predefined shape steer in two-dimensional (2D) space with a constant radius, and thereby require axial rotation to enable maneuvering and placement in 3D space. Rotation of a needle while the needle advances through tissue is not only difficult, but also increases the risk of tissue damage.

Active needles, on the other hand, can compensate for any possible misalignments via their actuation forces. Organ movements, physiological processes such as breathing, and human errors, are typical causes for these misalignments. With the help of the active needle's actuation and control, surgeons can guide their needle through a desired trajectory with increased accuracy.

Various research studies have suggested novel designs of active needles. One example includes an active segmented cannula with multiple stainless steel rings separated by pre-curved shape memory alloy (SMA) wire segments, with one SMA wire segment arranged between each pair of longitudinally segregated stainless steel rings. See Ayvali et al., Int. J. Rob. Res. 2012 April; 31(5): 588-603. Another example is disclosed by Ryu in a December 2012 Stanford University dissertation entitled "Optically Controlled Magnetic Resonance Imaging Compatible Needle" (available online at <http://purl.stanford.edu/ht443cf9111>), which provides an active needle using internal laser heating, conducted via optical fibers of a SMA actuator to produce bending in the distal section of the needle. One degree of freedom bending actuation was realized with a 1.37 mm outer diameter superelastic NiTi tube having a set of laser machined slits (rendering the tube uni-directionally flexible) and a 250 micron diameter NiTi SMA wire anchored at ends thereof to the tube by threading through two holes, to obtain localized needle tip bending.

The silent and robust actuation of SMAs, their biocompatibility, and their high power-to-mass ratio make them attractive for development of active medical devices. A key feature of SMAs is their ability to undergo a large seemingly plastic strain and subsequently recover the strain through the application of heat or load removal. The actuation behavior of SMAs is generated when an internal crystalline transformation (e.g., between Austenite (high temperature) and Martensite (low temperature) phases) happens with application of load or heat. Actuation happens when the Martensite (enlarged shape) transforms to the Austenite phase (smaller or parent shape).

Other types of steerable surgical devices incorporating multiple SMAs are disclosed in International Publication No. WO2018/183832A1, with the contents of such publication being incorporated by reference herein. An exemplary steerable surgical device includes a first tubular element, a second tubular element, a joint (e.g., at least a first joint), and a plurality of shape memory alloy wire elements. The first tubular element includes a first plurality of anchor points, and the second tubular element includes a second plurality of anchor points. The joint is arranged between the first tubular element and the second tubular element, and is configured to allow pivotal movement between the first tubular element and the second tubular element. The plurality of shape memory alloy wire elements extends across or through the first joint, is attached to the first plurality of anchor points, and is attached to the second plurality of anchor points. At least some shape memory alloy wire elements are independently actuatable to effectuate pivotal movement between the first tubular element and the second tubular element. In certain embodiments, separate actuation of the at least some shape memory alloy wire elements is configured to permit adjustment of pivot angles between the first tubular element and the second tubular element along at least two, or at least three, non-parallel planes.

Other surgical procedures utilize elongated tubular bodies that are inserted into patients (e.g., for intravascular use), with such tubular bodies being embodied in catheters, cannulas, guide wires, or the like.

Insertion of a narrow tubular body such as a flexible needle into a patent for performing a subcutaneous surgical procedure is a complex procedure for a physician. Typically, a surgeon will guide a needle to a target using an ultrasound image, which is susceptible to image noise, and it is frequently difficult to distinguish the needle from surrounding tissue unless there is precise alignment between the needle and an ultrasound probe. Moreover, mammalian (e.g., human) tissue is subject to deformation and movement.

When a needle is inserted, tissue will be deformed and the target may move. Due to factors such as limited visibility, limited tool maneuverability, susceptibility of needles to deflection, and variability in tissue, surgeons routinely rely on experience and tactile feedback to accomplish surgical goals. Regardless of the level of skill of the surgeon, however, it may be very challenging to manipulate a percutaneous needle within tissue to reach a desired target point while avoiding obstacles and undue tissue damage.

The art continues to seek improvement in systems and methods for controlling operation of steerable surgical devices to enhance their utility.

SUMMARY

Disclosed herein by way of certain exemplary embodiments is an autonomous system and method for controlling the operation of a steerable surgical device that includes a flexible joint positioned between first and second tubular elements, with the steerable surgical device being insertable into tissue of a mammalian body. An exemplary system includes a plurality of surgical device actuation elements, an imaging apparatus arranged external to a mammalian body, and at least one processor. The imaging apparatus generates signals used by the at least one processor to determine position of a tip of the steerable surgical device. A detected position of the steerable surgical device is used to identify deviation from a previously determined transit path, and an updated transit path generated by the at least one processor used for further advancement of the steerable surgical device through the tissue. The at least one processor is configured to generate a transit path between an insertion point and a target point, control the surgical device actuation elements to advance the steerable surgical device along one or more segments of the transit path, identify deviation of position relative to the transit path utilizing signals from the imaging apparatus and generate an updated transit path, and control the surgical device actuation elements to advance the steerable surgical device along at least one segment of the updated transit path. Systems and methods herein permit the at least one processor to control transit of the steerable surgical device through the tissue between the insertion point and the target point without human intervention. In certain embodiments, at least one processor is additionally configured to: (1) control at least one probe actuator to cause an imaging probe (of the imaging apparatus) to advance generally parallel to a segment of the transit path to a forward position ahead of the position of the tip and cause the imaging apparatus capture multiple images of tissue planes during such movement, and (2) control the imaging probe to retreat generally parallel to the segment of the transit path to a rearward position in which the tip is detectable by the imaging probe and cause the imaging apparatus to capture at least one image of a tissue plane in which the tip is visible.

In an exemplary aspect, the present disclosure relates to a system for autonomous movement of a steerable surgical device that includes a first tubular element, a second tubular element, and a joint therebetween, and that is insertable into tissue of a mammalian body. The system comprises a plurality of surgical device actuation elements, an imaging apparatus arranged external to the mammalian body, and at least one processor. The plurality of surgical device actuation elements comprises a first motor for controlling linear insertion of the steerable surgical device, a second motor for controlling rotary position of the steerable surgical device, and at least two actuators configured to effectuate pivotal movement between the first tubular element and the second tubular element. The at least one processor is configured to generate a transit path of the steerable surgical device through the tissue between an insertion point and a target point, and control the plurality of surgical device actuation elements to advance the steerable surgical device through the tissue along at least one segment of the transit path. The at least one processor is further configured to utilize signals obtained or derived from the imaging apparatus to identify a position of a tip of the steerable surgical device within the tissue, identify deviation of the position relative to the transit path, and generate an updated transit path. The at least one processor is additionally configured to control the plurality of surgical device actuation elements to advance the steerable surgical device through the tissue along at least one segment of the updated transit path from the position to the target point. The system is configured to cause the steerable surgical device to transit through the tissue between the insertion point and the target point under control of the at least one processor without human intervention.

In certain embodiments, the at least two actuators comprise shape memory alloy actuators. In certain embodiments, the at least two actuators comprises at least three actuators.

In certain embodiments, the imaging apparatus includes an imaging probe, and the system further comprises at least one probe actuator configured to move the imaging probe, wherein the at least one processor is configured to control the at least one probe actuator. In certain embodiments, the imaging apparatus comprises an ultrasound imaging apparatus, and the imaging probe comprises an ultrasound imaging probe.

In certain embodiments, the at least one processor is configured to generate the transit path and generate the updated transit path utilizing a Rapid-exploring Random Tree (RRT) algorithm with constraints on movement capabilities of the steerable surgical device.

In certain embodiments, the transit path and the updated transit path each avoid one or more defined obstacles within, proximate to, or bounding the tissue.

In certain embodiments, the transit path and the updated transit path each embody a path that minimizes damage to the tissue attributable to transit of the steerable surgical device through the tissue, while simultaneously avoiding one or more defined obstacles within, proximate to, or bounding the tissue.

In certain embodiments, the transit path and the updated transit path each embody a path that avoids one or more defined obstacles within, proximate to, or bounding the tissue, while also exhibiting at least one of the following features (i) or (ii): (i) minimizing damage to the tissue attributable to transit of the steerable surgical device through the tissue, or (ii) minimizing distance of transit of the steerable surgical device between the insertion point and the target point.

In certain embodiments, the steerable surgical device comprises an elongated flexible needle.

In another exemplary aspect, the present disclosure relates to a method for controlling movement of a steerable surgical device that includes a first tubular element, a second tubular element, and a joint therebetween, and that is insertable into tissue of a mammalian body, with the method comprising multiple steps. One step comprises generating, by at least one processor, a transit path of the steerable surgical device through the tissue extending from an insertion point to a target point, wherein the transit path avoids one or more obstacles. Another step comprises controlling, by the at least one processor, a plurality of surgical device actuation elements to advance the steerable surgical device through the tissue along at least one segment of the transit path. The plurality of surgical device actuation elements comprises a first motor for controlling linear insertion of the steerable surgical device, a second motor for controlling rotary position of the steerable surgical device, and at least two actuators configured to effectuate pivotal movement between the first tubular element and the second tubular element. Another step comprises identifying, by the at least one processor, position of a tip of the steerable surgical device within the tissue using signals received from an imaging apparatus. Another step comprises generating, by the at least one processor, an updated transit path for controlling movement of the steerable surgical device from a current position to the target point, wherein the updated transit path avoids the one or more obstacles. Another step comprises controlling, by the at least one processor, the plurality of surgical device actuation elements to advance the steerable surgical device through the tissue along at least one segment of the updated transit path. According to such a method, transit of the steerable surgical device through the tissue is controlled by the at least one processor without human intervention.

In another exemplary aspect, the present disclosure relates to a system for autonomous movement of a steerable surgical device that includes a first tubular element, a second tubular element, and a joint therebetween, and that is insertable into tissue of a mammalian body. The system comprises a plurality of surgical device actuation elements, an imaging apparatus arranged external to the mammalian body, at least one probe actuator configured to move an imaging probe of the imaging apparatus, and at least one processor. The at least one processor is configured to generate a transit path of the steerable surgical device through the tissue between an insertion point and a target point, and control the plurality of surgical device actuation elements to advance the steerable surgical device through the tissue along at least one segment of the transit path. The at least one processor is further configured to utilize signals obtained or derived from the imaging apparatus to identify a position of a tip of the steerable surgical device within the tissue, identify deviation of the position relative to the transit path, and generate an updated transit path. The at least one processor is additionally configured to control the at least one probe actuator to cause the imaging probe to advance generally parallel to a segment of the transit path to a forward position ahead of the position of the tip, and control the imaging apparatus to capture multiple images of tissue planes during such movement, including at least one image of a tissue plane ahead of the position of the tip in which the tip is not visible. The at least one processor is additionally configured to control the at least one probe actuator to cause the imaging probe to retreat generally parallel to the segment of the transit path to a rearward position in which the tip is detectable by the imaging probe, and control the imaging apparatus to capture at least one image of a tissue plane in which the tip is visible. The at least one processor is additionally configured to utilize signals obtained or derived from the imaging apparatus to generate an updated transit path; and to control the plurality of surgical device actuation elements to advance the steerable surgical device through the tissue along at least one segment of the updated transit path from the position to the target point. The system is configured to cause the steerable surgical device to transit through the tissue between the insertion point and the target point under control of the at least one processor without human intervention.

In another exemplary aspect, the present disclosure relates to a method for controlling movement of a steerable surgical device that is insertable into tissue of a mammalian body, wherein the method comprises multiple steps. One step comprises generating, by at least one processor, a transit path of the steerable surgical device through the tissue extending from an insertion point to a target point, wherein the transit path avoids one or more obstacles. Another step comprises controlling, by the at least one processor, a plurality of surgical device actuation elements to advance the steerable surgical device through the tissue along at least one segment of the transit path. Another step comprises utilizing, by the at least one processor, signals obtained or derived from an imaging apparatus to identify a position of a tip of the steerable surgical device within the tissue, and identify deviation of the position of the tip relative to the transit path. Another step comprises controlling, by the at least one processor, at least one probe actuator to cause an imaging probe to advance generally parallel to a segment of the transit path to a forward position ahead of the position of the tip, and control the imaging apparatus to capture multiple images of tissue planes, including at least one image of a tissue plane ahead of the position of the tip in which the tip is not visible. Another step comprises controlling, by the at least one processor, the at least one probe actuator to cause the imaging probe to retreat generally parallel to the segment of the transit path to a rearward position in which the tip is detectable by the imaging probe, and control the imaging apparatus to capture at least one image of a tissue plane in which the tip is visible. Another step comprises utilizing, by the at least one processor, signals obtained or derived from the imaging apparatus to generate an updated transit path. Another step comprises controlling, by the at least one processor, the plurality of surgical device actuation elements to advance the steerable surgical device through the tissue along at least one segment of the updated transit path from the position to the target point. According to such a method, transit of the steerable surgical device through the tissue is controlled by the at least one processor without human intervention.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the certain exemplary embodiments in association with the accompanying drawing figures.

BRIEF DESCRIPTION OF DRAWINGS

FIG. 8A is a perspective view of a modeled active needle including first through fourth tubular body members with soft elastic joints arranged between different body member, with through-holes defined through the body members and joints to permit passage of shape memory alloy wire actuators.

FIG. 8B is a perspective view of one of the elastic joints of FIG. 8A.

DETAILED DESCRIPTION

Figure 1:
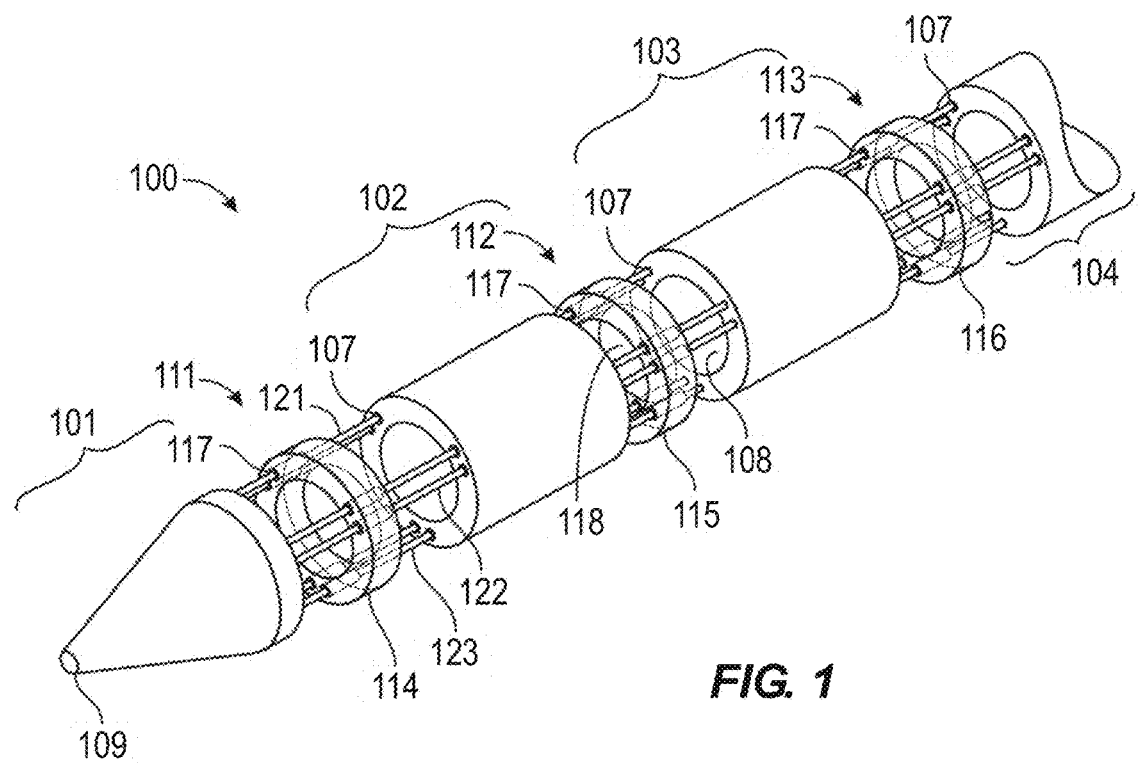
FIG. 1 is an exploded perspective view of a steerable surgical device useable with embodiments herein, including shape memory alloy wire elements extending through longitudinal bores defined in tubular elements and joint elements of the steerable surgical device.

An autonomous system and method for controlling the operation of a steerable surgical device are disclosed herein, with the steerable surgical device including a flexible joint positioned between first and second tubular elements, and being insertable into tissue of a mammalian body. An exemplary system according to the present disclosure includes a plurality of surgical device actuation elements, an imaging apparatus arranged external to a mammalian body, and at least one processor. The imaging apparatus generates signals used by the at least one processor to determine position of a tip of the steerable surgical device. A detected position of the steerable surgical device is used to identify deviation from a previously determined transit path, and an updated transit path generated by the at least one processor used for further advancement of the steerable surgical device through the tissue. In certain embodiments, the at least one processor is additionally configured to: (1) control at least one probe actuator to cause an imaging probe (of the imaging apparatus) to advance generally parallel to a segment of the transit path to a forward position ahead of the position of the tip and cause the imaging apparatus capture multiple images of tissue planes during such movement, and (2) control the imaging probe to retreat generally parallel to the segment of the transit path to a rearward position in which the tip is detectable by the imaging probe and cause the imaging apparatus to capture at least one image of a tissue plane in which the tip is visible.

Conventional needle-based procedures involve a surgeon guiding a needle inside the tissue to reach a target position. Subject matter disclosed herein enables needle transit through tissue to be mostly or fully automated (e.g., robotic), thereby eliminating the role of human practitioners and errors attributable to humans when performing a conventional procedure. In certain embodiments, initial insertion of a needle is performed by a human practitioner, and with subsequent transit from the insertion point to the target point being controlled solely by an automated system as disclosed herein. The disclosed needle insertion system tracks the needle tip with a robot-driven ultrasound probe, and the tip of a needle is located with image capture and processing steps disclosed herein.

Introduction to Steerable Surgical Devices

Aspects of the disclosure may be understood following introduction of steerable surgical devices incorporating multiple shape memory alloy (SMA) actuators. A steerable surgical device includes a flexible joint positioned between first and second tubular elements, with multiple shape memory alloy wire elements extending across or through the joint being independently actuatable to effectuate pivotal movement between the first and second tubular elements along multiple non-parallel planes. A SMA is an alloy that "remembers" an original state and that, following deformation, returns to its pre-deformed state when actuated (e.g., electric current, heat, magnetic field, etc.). In certain embodiments, multiple (e.g., two, three, or more) SMA wire elements are attached to circumferentially-spaced first anchor points of the first tubular element and circumferentially-spaced second anchor points of the second tubular element, and are independently actuatable to effectuate pivotal movement between the first and second tubular elements. The SMA wire elements predictably and reliably contract relative to the current transmitted therethrough. In this way, the steerable surgical device provides for precise multi-dimensional pivotal movement of the first tubular element relative to the second tubular element. For example, the presence of at least three properly configured and independently actuatable shape memory alloy wire elements may permit adjustment of pivot angles between the first tubular element and the second tubular element along at least three non-parallel planes. This exacting control and precision allows the steerable surgical device to be fed through and/or inserted into tissue of a mammalian subject for a variety of medical applications.

Figure 2:
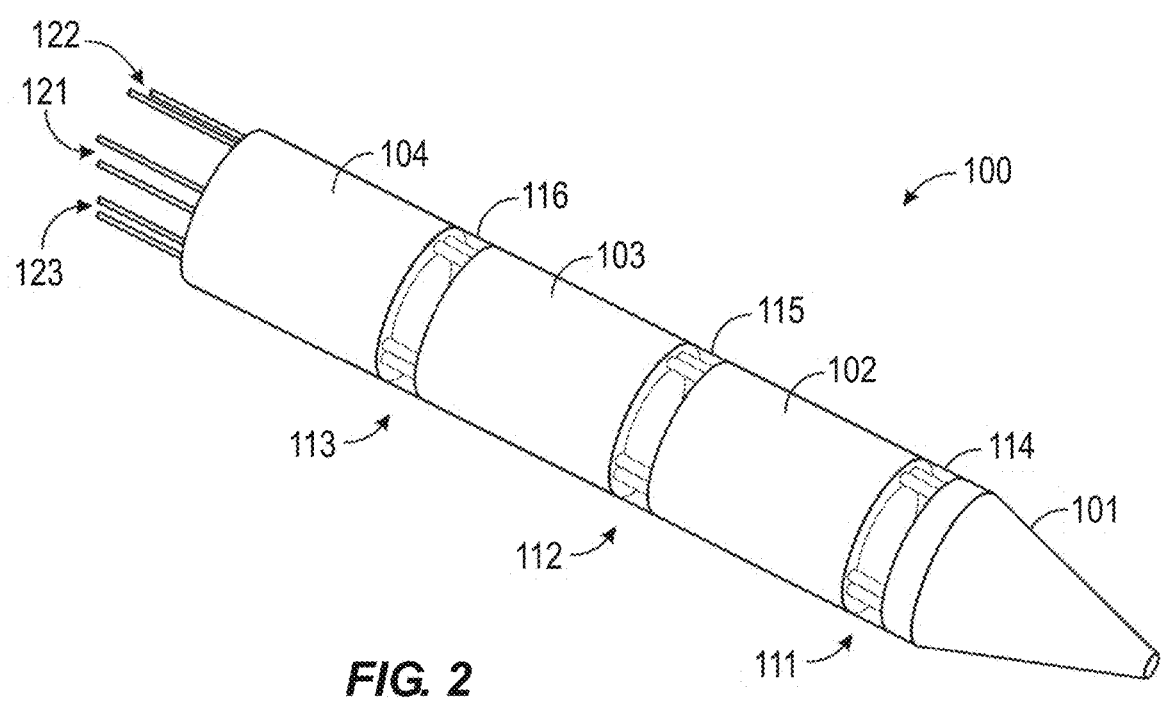
FIG. 2 is a perspective view of the steerable surgical device of FIG. 2 in an assembled state.

An exemplary steerable surgical device is illustrated in FIGS. 1 and 2, with such figures being excerpted from International Application No. PCT/US2018/025380 filed on Mar. 30, 2018 and subsequently published as International Publication No. WO2018/183832A1. FIG. 1 is an exploded perspective view of a steerable surgical device 100 useable with certain embodiments herein, including SMA wire elements 121-123 extending through longitudinal bores 107 defined in at least some tubular elements 102-104, and extending through longitudinal bores 117 defined in flexible elements 114-116 of the steerable surgical device 100. The steerable surgical device 100 includes first through fourth tubular elements 101-104, with the first tubular element including a needle tip 109 and having a substantially conical shape. Each flexible element 114-116 is positioned between, and forms a joint 111-113 between, a different pair of tubular elements 101-104. Each tubular element 101-103 may include an interior cavity 108, and each flexible element 114-116 likewise may include an interior cavity 118 such that the flexible elements 114-116 may be substantially annular in shape. As shown in FIG. 1, the tubular elements 102-104 each include three closely-spaced pairs of longitudinal bores 107, with a center of each pair of longitudinal bores 107 being about 120 degrees apart from a center of each other pair of longitudinal bores 107. Likewise, the flexible elements 114-116 each include three closely-spaced pairs of longitudinal bores 117, with a center of each pair of longitudinal bores 117 being about 120 degrees apart from a center of each other pair of longitudinal bores 117 defined through the flexible elements 114-116. The respective bores 107, 117 defined in the tubular elements 102-104 and defined in the flexible elements 114-116 are configured to permit the passage of SMA wire elements 121-123 that serve as actuators. Providing SMA wire actuators completely enclosed inside the steerable surgical device 100 (e.g., within bores 107, 117 defined in the tubular elements 102-104 and defined in the flexible elements 114-116) avoids contact between the SMA wire elements 121-123 and tissue, thereby preventing the heating of SMA elements 114-116 from causing tissue damage when the steerable surgical device 100 is used inside a patient's body.

In certain embodiments, a first end of each SMA wire element 121-123 may be inserted (in a direction generally toward the needle tip 109) through a longitudinal bore 107 defined in the fourth tubular element 104, through a longitudinal bore 117 defined in the third flexible element 116, through a longitudinal bore 107 defined in the third tubular element 103, through a longitudinal bore 117 defined in the second flexible element 115, through a longitudinal bore 107 defined in the second tubular element 102, through a longitudinal bore 117 defined in the first flexible element 114, and into an interior of the first tubular element 101 to be received by an anchor (e.g., loop, post, or the like), and then returned in reverse order (away from the needle tip 109) through a paired (closely spaced) longitudinal bore 117 defined in the first flexible element 114, through a paired (closely spaced) longitudinal bore 107 defined in the second tubular element 102, and so on, until the respective SMA wire element 121-123 exits the fourth tubular element 104. In this manner, each pair of longitudinal bores 107 in the tubular elements 102-104 and each pair of longitudinal bores 117 in the flexible elements 114-116 receives a single SMA wire element 121-123, such that first and second ends of each SMA wire element 121-123 may be accessible at an end of the steerable surgical device 100 distal from the needle tip 109 (i.e., as shown in FIG. 2). Actuation of a single SMA wire element 121-123 may cause each joint 111-113 to pivot along one deflection plane. Individually controllable actuation of the SMA wire elements 121-123 may permit the pivotal movement of the needle tip 109 along at least three planes, such that three-dimensional pivotal movement of the needle tip 109 is enabled.

FIG. 2 is a perspective view of the steerable surgical device 100 of FIG. 1 in an assembled state, showing the flexible elements 111-113 arranged between and in contact with different pairs of the tubular elements 101-104, and showing both ends of each of three shape memory alloy wire elements 121-123 extending outward beyond the fourth tubular element 104.

Elements of the steerable surgical device 100 of FIGS. 1 and 2 (e.g., other than the shape memory alloy elements 121-123) may be produced by any suitable means, including extrusion, 1D printing, or the like. In certain embodiments, the tubular elements 101-104 may comprise polymeric material (optionally reinforced) such as fluoropolymers, polyolefins, polyamides, or the like.

The above-described steerable surgical device 100 of a clinically feasible size is insertable into tissue of a mammalian body, and is capable of 3D manipulation and control to reach a target location via robotic instruments (e.g., utilizing at least one processor configured to execute machine-readable instructions embodied in software, firmware, or a combination thereof). In certain embodiments, the at least one processor may be embodied in one or more computing devices.

The unique characteristics of SMAs known as Shape Memory Effect (SME) and pseudo-elasticity (PE), along with desirable material properties such as corrosion resistance and biocompatibility, plus their high actuation energy densities, have made SMAs a suitable choice for use in actuating active needles. Various heating and cooling techniques to drive SMAs include electrical heating (Joule heating) or inductive heating, air cooling, forced air/liquid cooling, etc. Another distinct advantage of SMAs as actuators is their self-sensing capabilities. Along with strain recovery, the electrical resistance of a SMA actuator alters notably during the transformation between austenite to martensite or vice-versa. This phenomenon can be applied to design a feedback positioning control by measuring electrical resistance variation through SMA actuators to estimate the actuation strain. Due to the correlation between the actuation strain and the electrical resistance (which may be determined quantitatively through characterization experiments), SMAs can be used as smart actuators.

Figure 3A:
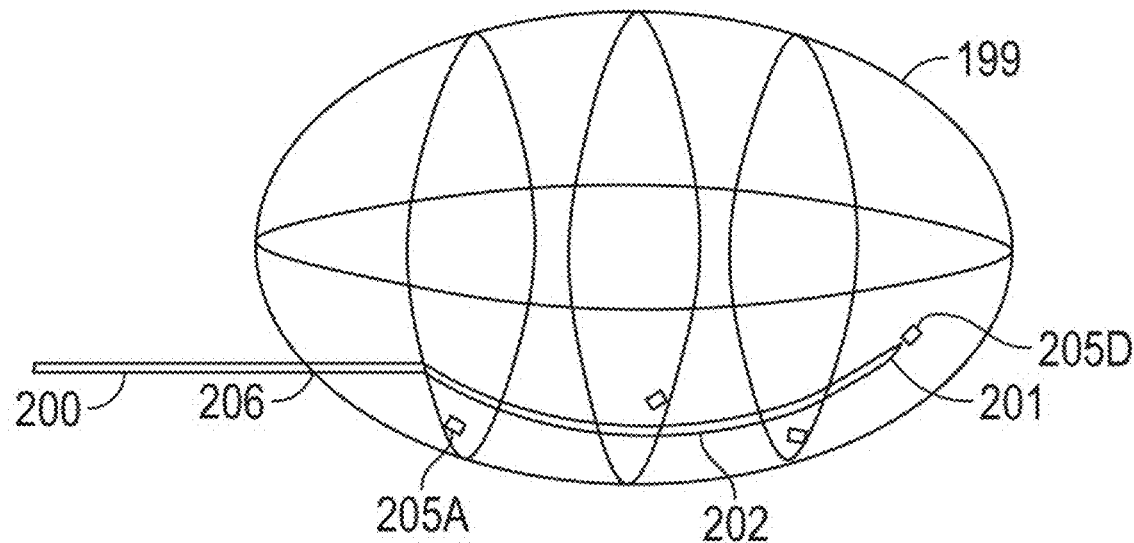
FIG. 3A is a schematic view illustration of a conventional flexible needle being manipulated within an organ proximate to multiple specific targets following introduction into the organ through a single insertion point.
Figure 3B:
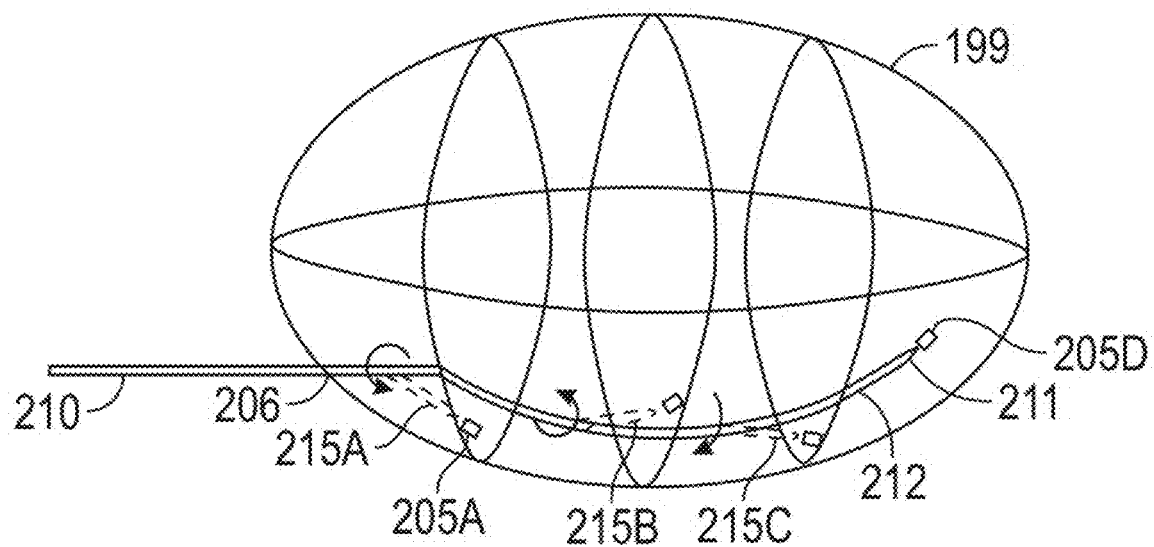
FIG. 3B is a schematic view illustration of a steerable surgical device according to one embodiment of the present disclosure being manipulated within an organ to directly access multiple specific targets (with intermediate trajectories shown in dashed lines) following introduction into the organ through a single insertion point.

FIGS. 3A and 3B permit comparison of a conventional flexible needle and a steerable surgical needle-type device following insertion into an organ through a single insertion point. FIG. 3A is a schematic view illustration of a conventional flexible needle 200 (having a flexible end portion 202 in a curved configuration proximate to a needle tip 201) being manipulated within an organ 199 proximate to multiple specific targets 205A to 205D following introduction of the needle 200 into the organ 199 through a single insertion point 206. The flexible needle 200 gets near, but does not directly access, several of the specific targets 205A to 205D within the organ 199.

FIG. 3B is a schematic view illustration of a steerable surgical needle-type device 210 (having a steerable end portion 212 shown in a curved configuration proximate to a needle tip 211) according to an embodiment of the present disclosure being manipulated within an organ 199 to directly access multiple specific targets 205A to 205D following introduction of the steerable surgical needle-type device 210 into the organ 199 through a single insertion point 206. Intermediate trajectories 215A to 215C of the needle tip 211 are shown in dashed lines. As shown in FIG. 3B, use of a steerable surgical needle-type device 210 and multiple intermediate trajectories permits the steerable surgical needle-type device 210 to directly access each of the specific targets 205A to 205D. Such capability is facilitated by the reliability, predictability, and precision of the SMA elements.

Figure 4A:
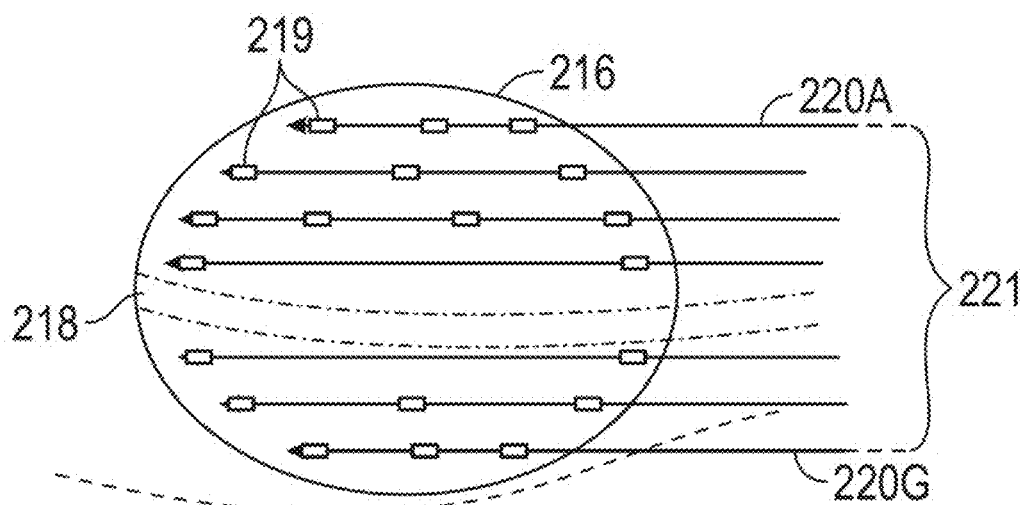
FIG. 4A is a schematic view illustration of paths taken by a conventional straight needle during a process of delivering radioactive seeds to multiple target sites within a prostate gland through seven insertion points.
Figure 4B:
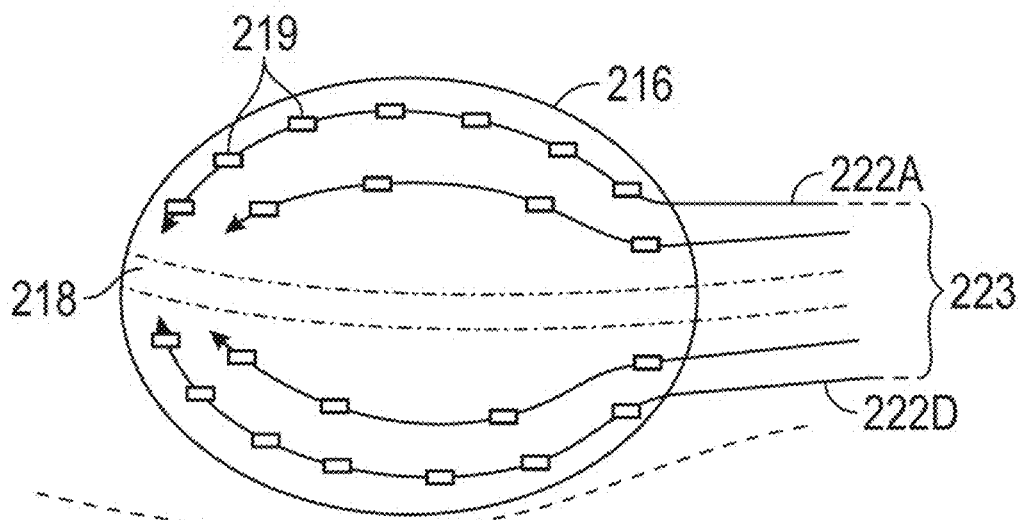
FIG. 4B is a schematic view illustration of paths taken by a steerable surgical device according to one embodiment of the present disclosure during a process of delivering radioactive seeds to a similar number of target sites within a prostate gland through four insertion points.

FIGS. 4A and 4B permit comparison of operation of a conventional straight needle and a steerable surgical needle-type device through multiple insertion points in a surgical process. FIG. 4A is a schematic view illustration of needle paths 220A to 220G taken by a conventional straight needle during a process of delivering radioactive seeds through several insertion points to multiple target sites 219 within a prostate gland 216, which surrounds a urethra 218 and is positioned proximate to a rectal wall 217. Needle paths 220A to 220G (shown as seven in number) are selected to avoid puncture of the urethra 218 but still distribute radioactive seeds to widely distributed target sites 219. To provide the desired distribution of radioactive seeds using a conventional straight needle, a large aggregate puncture area 221 is required.

FIG. 4B is a schematic view illustration of paths 222A to 222D taken by a steerable surgical device according to one embodiment of the present disclosure during a process of delivering radioactive seeds to a similar number of target sites 219 within a prostate gland 216 (also surrounding a urethra 218 and positioned proximate to a rectal wall 217), but through a smaller number of insertion points (e.g., four in number) encompassing a smaller aggregate puncture area 223 relative to the puncture area 221 of FIG. 4A. The number of insertion points (e.g., puncture areas) is decreased because the steerable surgical device is able to access a wider range of areas from each puncture. The ability to deliver a similar distribution of radioactive seeds to a prostate gland 216 through a smaller aggregate puncture area 223 while avoiding sensitive structures (e.g., urethra 218 and rectal wall 217) may provide beneficial effects such as reduced risk of infection and improved healing time.

System for Autonomous Movement of Steerable Surgical Device

Figure 5A:
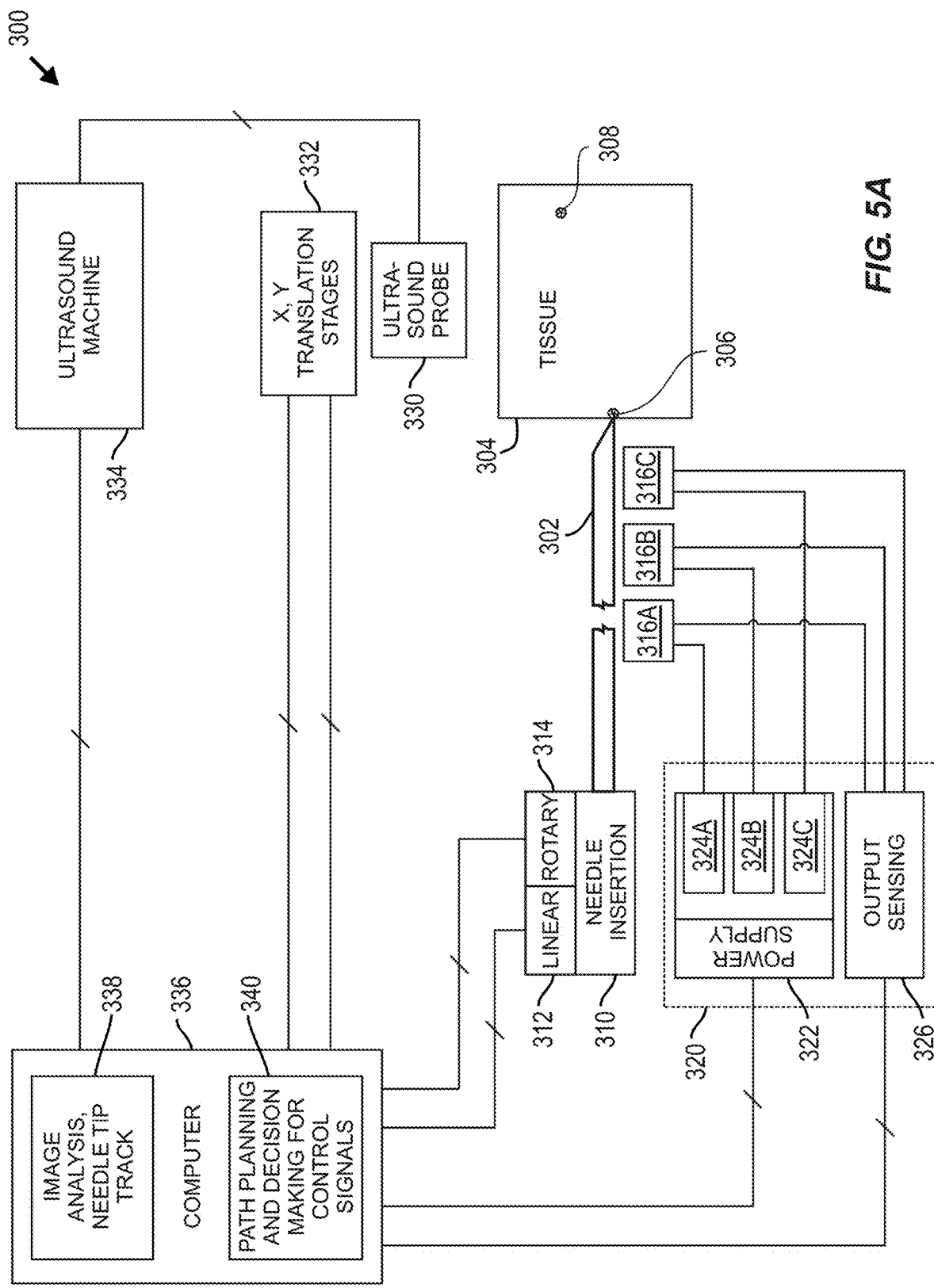
FIG. 5A is a schematic diagram showing interconnections between various elements of a system for autonomous movement of a steerable surgical device that is insertable into tissue of a mammalian body according to one embodiment of the present disclosure.

FIG. 5A is a schematic diagram showing interconnections between various elements of a system 300 for autonomous movement of a steerable surgical device 302 that is able to be inserted into tissue 304 of a mammalian body, according to one embodiment of the present disclosure. The tissue 304 is shown at lower right, with an insertion point 306 and a target point 308 (which is internal to the tissue 304) marked therein. Just outside the tissue 304 proximate to the insertion point 306, a steerable surgical device (e.g., including or consisting of a needle) 302 is coupled with a needle insertion apparatus 310 that includes a first motor 312 for controlling linear insertion of the steerable surgical device 302, and a second motor 314 for controlling rotary position of the steerable surgical device 302. Further illustrated are three SMA actuators 316A-316C (that may each embody a NiTi wire) coupled to a direct current (DC) programmable power supply 320 including a power supply module 322 and an output sensing module 326. Each SMA actuator 316A-316C is coupled to a different gain (output) 324A-324C of the power supply module 322 for independent control of the supply of electric current to the shape memory alloy actuators 316A-316C. The output sensing module 326 is used to measure voltage and current flowing through each SMA actuator 316A-316C. It is to be appreciated that the shape memory alloy actuators 316A-316C may be arranged at different angular positions relative to the steerable surgical device 302 (e.g., generally one hundred twenty degrees apart such as shown in FIGS. 1 and 2). The SMA actuators 316A-316C are configured to effectuate pivotal movement between tubular elements (not shown) of the steerable surgical device 302 responsive to application of electric current to the SMA actuators 316A-316C. An ultrasound probe 330 is arranged proximate to the tissue 304, with associated x and/or y translation stages 332 arranged to permit the ultrasound probe 330 to move relative to the tissue 304. The ultrasound probe 330 is coupled to an ultrasound imaging machine 334 (e.g., an Chison ECO5 ultrasound machine in certain embodiments). A computer 336 (e.g., incorporating at least one processor) is coupled with the above-mentioned components. As noted, the computer 336 provides multiple functions, wherein specific functions may be provided by modules such as an image analysis and needle tip tracking module 338 (utilizing images received from the ultrasound machine 324) and a path planning and decision making module 340 that may generate control signals. The computer 336 provides command signals to drive the first and second motors 312, 314, as well as the shape memory alloy actuators 316A-316C (by way of the power supply module 322 with dedicated current gains 324A-324C) to effectuate movement of the steerable surgical device 302 in the tissue 304 with steering along a path between the insertion point 306 and the target point 308. Such path may include one or more curves, bends, and/or twists, and the steerable surgical device 302 may be actuated to change its shape (e.g., curvature) during transit with the tissue 304. Signals indicative of or derived from voltage and/or current flowing through the shape memory alloy actuators 316A-316C are supplied from the output sensing module 326 to the computer 336. The computer 336 also provides command signals to the x and/or y translation stages 332 to move the ultrasound probe 330 relative to the tissue 304.

Figure 5B:
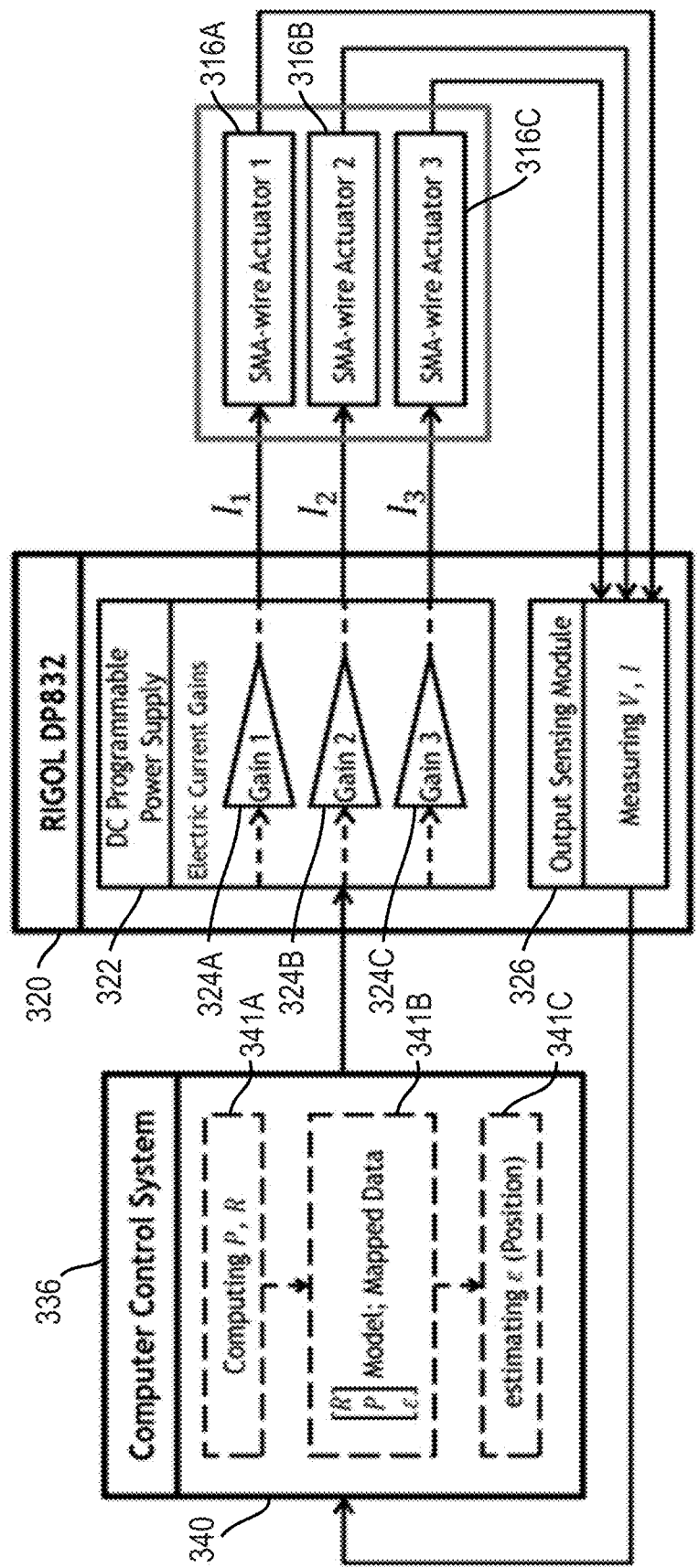
FIG. 5B is a schematic diagram showing a more detailed implementation of a portion of the system of FIG. 5A used to control the shape memory alloy actuators.

FIG. 5B is a schematic diagram showing a more detailed implementation of a portion of the system 300 of FIG. 5A used to control the SMA wire actuators 316A-316C, including SMA self-sensing resistance feedback control. The illustrated components include the SMA actuators 316A-316C, the DC programmable power supply 320, and a portion of the computer 336 including the path planning and decision making module 340. As shown, the DC programmable power supply 320 may be embodied in a Rigol DP832 programmable power supply 320, including a power supply module 322 and an output sensing module 326. The power supply module 322 includes three independent outputs (e.g., gains) 324A-324C configured to independently supply variable current to the shape memory alloy actuators 316A-316C. The output sensing module 326 measure voltage (V) and current (I) values flowing through each SMA actuator 316A-316C, and supplies signals indicative of these values to the path planning and decision making module 340 of the computer 336. The path planning and decision making module 340 may include a first submodule 341A configured to receive real-time measurements and compute electric power (P) and electric resistance (R) of the shape memory alloy actuators 316A-316C; a second submodule 341B including stored numerically mapped strain-power-resistance characteristics data for each of the SMA actuators 316A-316C, and a third submodule 341C configured to use the computed values and strain-power-resistance characteristics data to estimate position (c) of the SMA actuators 316A-316C.

Having introduced the components of FIG. 5B, a control scheme for actuation of the shape memory alloy actuators 316A-316C will now be described. The control scheme controls the amplitude of the input electric current actuation signals, while taking online measurements of the electric current and voltage across the SMA actuators 316A-316C to monitor the electric resistance and the supplied electrical power using Ohm's law, for the SMA actuators 316A-316C. The computer 336 derives estimates of actuator position (strain) by assessing the strain-power-resistance characteristics mapped data. The control scheme modifies the gain factor of the input signal to actuate and control the SMA-wire actuators. Tunable high gain and low gain factors regulate the amplitude of the input electric current actuation signals. The high-gain signal serves as the actuation heating cycle, delivering electrical power to actuate the SMA actuators 316A-316C (Joule heating); while the low-gain signal is a low nonzero amplitude signal that serves as the actuation cooling cycle due to the higher rate of cooling by natural convection compared to the power generation by the low amplitude electric current signal in each SMA actuator 316A-316C. The low amplitude current signal is intended to prevent singularities in measuring the electric resistance of the SMA actuators 316A-316C by Ohm's law (i.e., as current goes to zero, the limit of resistance is infinity). The control system exploits self-sensing capabilities of the shape memory alloy actuators 316A-316C, taking the real-time measurements of the electric resistance and electric power of the SMA actuators 316A-316C, in tunable time intervals, to obtain estimations of the actuators displacement by the assessments of the actuators numerically mapped strain-power-resistance characteristics data. The electric power is measured to determine the current state of the actuation duty, i.e. heating and cooling cycles. Due to the hysteresis in the shape memory alloys, measuring the electric resistance does not reveal the current state in heating or cooling paths in actuation duties.

A Picture Archiving and Communication System (PACS) was developed to transfer the images from the ultrasound machine to a computer based on Digital Imaging and Communications in Medicine (DICOM) protocol. The computer opens a port through a Python software on Pynetdicom, and Pydicom to transfer and decompress the images. The software automatically decompress a new transferred file to '.png' format images for further processing. Images transferred to the computer may be used for analysis and decision making, to provide a feedback signal for control of movement of the steerable surgical device within the tissue, and to provide a feedback signal for path planning (e.g., generating one or more updated paths for intended transit of the steerable surgical device).

Processor-Based Path Planning, Needle Control, Probe Control, and Position Tracking The foregoing system is configured to direct movement of a steerable surgical device (e.g., a steerable needle) within the tissue toward a target point while avoiding obstacles (e.g., sensitive organs and structures, organ boundaries, etc.). The computer (e.g., at least one processor) may be configured to implement the following: (1) a path planning program to generate an optimized path with minimum tissue rupture to reach the target, (2) a control program to move the needle, (3) a control program to move the ultrasound probe relative to the tissue, and (4) a needle position tracking program to receive images from the ultrasound machine, process the images to find the actual position of the needle tip, and calculate deviation of the needle tip position from the planned path. These four items (1) to (4) are detailed below.

(1) Path Planning Program:

A path planning program generates a 2D path for a needle to navigate inside the tissue and reach the target. In certain embodiments, a path planning program may be implemented as modified version of an open source Python code by Atsushi Sakai utilizing a system incorporating the motors and shape memory alloy actuators according to FIG. 5 to enable the needle to maneuver inside the tissue. A technical benefit of the path planning program in combination with the high degree of maneuverability provided by the needle (e.g., with three shape memory alloy actuators as well as linear travel and rotary positional control) is that it enables an optimized path for navigation that imparts minimal rupture to the tissue while still avoiding predefined obstacles within the tissue.

In certain embodiments, the path of a needle (or other steerable surgical device) may be updated numerous times along an insertion path (e.g., at every 5 mm of insertion depth, or another length threshold) based on deviation of the actual location of the needle tip relative to a transit path. Calculation of deviation error may be performed based on a needle position tracking program, of which one embodiment is described hereinafter.

Set out below is a step-by-step algorithm for path planning that may be used according to certain embodiments, utilizing as inputs an Angle the Needle can create (AN), and needle Insertion Depth (ID).

0. $P_0$=Insertion Point, P1=Target point, P0=Node (wherein P0 initially equals $P_0$)
1. Choose RC=Random Coordinates
2. Find the closest node to RC
3. Check "angle of (P0, RC, P1)<AN"
    IF YES:
        3.1. Do the extension by length of ID, by the angle defined in Step 3
        3.2. Check "the extended point is not colliding with the obstacles"
            IF YES:
                3.2.1. Pick a new node from the extended point
                3.2.2. If the distance to target is in an acceptable range
                    IF YES: Break the process
                    IF NO: Go back to Step 1
            IF NO: Go back to Step 1
    IF NO: Go back to Step 1.

(2) Control Program to Move the Needle:

A control program sends appropriate command signals to the motorized stages (linear and rotary) and the needle's shape memory alloy actuators move the needle inside the tissue based on a generated transit path (outlined in item (1) above).

(3) Control Program to Move the Ultrasound Probe:

Once the needle travels inside the tissue for 5 mm, another control program integrated with the ultrasound feedback can move the ultrasound imaging probe on top of the tissue to find the needle tip. This program ensures that the ultrasound imaging probe is taking images exactly from the tip of the needle instead of from the shaft of the needle. It should be noted that the 2D images of the ultrasound may be taken in a plane perpendicular to the needle insertion direction (i.e., x-direction). The control program moves the translation stage(s) and the associated ultrasound imaging probe forward, and captures images at every 0.5 mm of direction depth; meanwhile, a continuous search is being performed on each image until the needle tip disappears from the images. Finally, the program moves the probe one frame backward to look at the needle tip. Restated, the probe actuator is controlled to cause the imaging probe to advance generally parallel to a segment of the transit path to a forward position ahead of the position of the tip, and the imaging apparatus is controlled to capture multiple images of tissue planes during such movement, including at least one image of a tissue plane ahead of the position of the tip in which the tip is not visible. Thereafter, the probe actuator is controlled to cause the imaging probe to retreat generally parallel to the segment of the transit path to a rearward position in which the tip is detectable by the imaging probe, and the imaging apparatus is controlled to capture at least one image of a tissue plane in which the tip is visible.

This control of movement and imaging of the ultrasound probe is expected to provide improved accuracy compared to the methods normally used by other research groups, where a needle-tissue interaction model is used to predict the position of the needle tip at each stage of insertion, and move the probe accordingly. The inventive program eliminates the uncertainties and the consequent errors of the needle-tissue interactions models, although increasing the operation time to some extent.

(4) Needle Position Tracking Program:

A needle position tracking program provides the real position of the needle inside the tissue at each stage of the insertion. It receives the images from the ultrasound machine, processes the images to locate the needle tip, finds the needle tip at each stage of insertion, calculates its deviation from the planned path, and provides it to the path planning program (i.e., referring to item (1) above).

To receive images from the ultrasound machine, a PACS server is created to connect the ultrasound machine to a computer, and images are transferred via a Digital Imaging and Communications in Medicine (DICOM) port. To receive the frames, the Pynetdicom3 package is used and modified based on the type of images and the PACS server requirements. The transmitted images are in ".dcm" format, which will be later converted to ".png" format for further processing using Pydicom, PILOW, and Numpy packages.

To find the needle tip in the images, image processing is used. A search may be done on 2D images captured by the ultrasound to find and coordinate the needle tip. The converted images show an inserted needle in a tissue. To track the needle tip, the method of 2D tracking of objects in Maghsoudi et al., "Superpixels Based Marker Tracking vs. Hue Thresholding in Rodent Biomechanics Applications" (arXiv:1710.06473v4 [cs.CV] 28 May 2018, available online at <https://arxiv.org/pdf/1710.06473.pdf>) is modified and used.

Set out below is a first step-by-step algorithm to search for the needle tip between the images captured by the ultrasound machine and transferred to the computer.

0. i=1
1. Load frame i
2. Manually locate the initial tip of the needle
3. i=i+1
4. Load frame i
5. Generate Super Pixel (SP)
6. Find the best SP based on the geometry, shape, and stiffness of the needle, and its previous position
7. If the matching score is less than a defined threshold, break the process: frame i−1 has the tip of the needle
8. Go back to step 3.

Superpixels are well known in the art of image processing. Superpixels group perceptually similar pixels to create visually meaningful entities while significantly reducing the number of primitives for subsequent processing steps. Publicly available superpixel algorithms have become standard tools in low-level vision.

Calculating the needle tip deviation from the planned path and providing it for path planning was introduced previously. Identifying the tip of the needle inside the tissue at each stage of the insertion is important to calculate its deviation from the pre-planned path. This step uses the tracked position of needle tip from the 2D ultrasound images to calculate the required steering for the needle to maintain the planned path.

Advanced Needle Tracking System

After development of the needle tracking algorithm outlined hereinabove, an advanced needle tracking system and method were developed. A discussion of image segmentation is provided below, followed by a discussion of the advanced needle tracking system and method.

1. Segmentation

Normalized cuts, the mean shift algorithm, graph-based methods, SLIC superpixels, and optimization-based superpixels are all modern methods with which to segment regions of an image. Superpixels contract and group uniform pixels which make a more natural and perceptually meaningful representation of the input image, as compared to single pixels. The use of superpixels was selected because their over- and under-segmentation criteria and performance are well-suited to the task of segmenting the paws. Simple Linear Iterative Clustering (SLIC) is used in certain embodiments because it generates superpixels faster than other methods. As the size of images is constant in various embodiments, the number of superpixels becomes the critical parameter. The speed of the superpixels algorithm depends largely on this number of superpixels and the size of the image. In certain embodiments, the size of superpixels may be adjusted based on the size of needle and image resolution.

SLIC performs a local clustering of pixels based on their color similarity and proximity in the image plane. SLIC may be performed in the five-dimensional [labxy] space, where [lab] is the pixel color vector in the CIELAB color space, and xy is the pixel position. Methods for generating SLIC superpixels are disclosed, for example, in Achanta et al., "SLIC Superpixels," EPFL Technical Report 149300, June 2010.

2. Tracker

For clarity, tracking system is described in three parts: first, manual initialization for the first frames; second, a typical needle tracker algorithm, referred as the "general tracker," and finally, adjusting and optimizing the tracked coordinates.

2.1. Initialization

The major role of this simple step is to find the tip of needle coordinates in the first 2D ultrasound image following by extracting some features to aid in finding the best-matched segment amongst the segments for the subsequent images. Therefore, the superpixels are generated based on an initial value for the number of superpixels, and the user is asked to zoom in, using a rectangle zoom tool in the software, for a better resolution and click on the tip of needle. This means that the initialization consists of one round of clicking on the tip of needle by user and further processing as described in Algorithm 1.

From this step, the initial grey scale value, $G_{D[i]}$ is extracted in equation 1, where i shows image number and it is 1 for the first image. This value would remain constant unless the user requests to modify the tracking parameters. In the case that a user asks for changes, these values could be updated by new values for that image. This value is used to extract features for the next images, see equation 1. The initialization process can be repeated for the second frame of each camera, or be bypassed.

To simplify and speed up the process, a window is considered for the other images to limit the region looking for the needle. This window can be adjusted and optimized based on the "optimization" step.

2.2. General Tracker

In a first step, a lowpass filter is used to reduce noise in the image. Focus is subsequently made on a window, for example 100*100 pixels, showing the region of interest, given by a 2D coordinate predicted by a 2D Kalman Filter. The Kalman Filter (KF) model assumes that a state of a system for frame number n evolves from the prior state at frame number n−1. It has been used frequently for different applications to predict a location of object based on its previous locations.

It should be noted that the KF is designed with a constant speed in our method. This point has 2D coordinates of $[U_{P[i]}, V_{P[i]}]$ for frame number i. Then, superpixels are generated for the "sub-images" and four intensity and location features are extracted, according to the following Equation Group 1:

$$F_{1[i,j]} = |\text{Mean}(G_{SP[i,j]}) - \text{Mean}(G_{D[0]})|$$

$$F_{2[i,j]} = |\text{Mean}(G_{SP[i,j]}) - \text{Mean}(G_{D[i-1]})|$$

$$F_{3[i,j]} = \text{Sqrt}([\text{Mean}(U_{SP[i,j]}) - U_{B[i]}]^2 + [\text{Mean}(V_{SP[i,j]}) - V_{B[i]}]^2)$$

$$F_{4[i,j]} = \text{Sqrt}([\text{Mean}(U_{SP[i,j]}) - U_{P[i-1]}]^2 + [\text{Mean}(V_{SP[i,j]}) - V_{P[i-1]}]^2) \quad (1)$$

where j and i are the superpixel number (for all superpixels in a "sub-image" or region of interest defined by the window) and the image number. $SP_{[i,j]}$, D[i], and P[i] are the superpixel number j for the image number i, the detected needle tip for frame number i, and the predicted position of needle for frame number i. $F_{1[i,j]}$ to $F_{4[i,j]}$ are the four features corresponding to $SP_{[i,j]}$. B and P are the coordinates of the bottom left and the center of the "sub-image" in the camera image planes. Therefore, the term $\text{Mean}(G_{SP[i,j]})$ means the average of gray level intensity values of pixels in j-th superpixel of i-th frame It should be noted that the SP denotes superpixels for the current frame (in other words, superpixels candidates for being a needle in frame number and the term j is an index to test all the superpixels in the window. On the other hand, D is the detected superpixel from the previous frame (frame number i−1). After the segmentation, tracking, and the optimization, the best superpixel is assigned to D[i,j] for image number i, as illustrated in Algorithm 2. In addition, since a superpixel has many pixel members, and each pixel has coordinates in the image in the U and V directions, wherein $U_{SP}$, $V_{SP}$, $U_P$ and $V_P$ are arrays of scalars. Therefore, $\text{Mean}(U_{SP})$ refers to calculation of the average of coordinates in a direction for all for the pixels associated with that superpixel.

Four features are normalized ($N_{k[i,j]}$ where k shows the feature number between one to four) according to the following Equation 2:

$$N_{k[i,j]} = 1 - \frac{F_{k[i,j]} - \min(F_{k[i,\forall j]})}{\max(F_{k[i,\forall j]}) - \min(F_{k[i,\forall j]})} \quad (2)$$

The normalized features are weighted based on the importance of features using the arrays according to Equation 3 (with specific values provided as an example only):

$$\text{Weights} = [2,1,2,2] \quad (3)$$

where Weights is the weights to calculate a score for the needle segments, respectively.

2.3. Optimization and Adjustment of Window Size

The adjustment process includes an algorithm (Algorithm 1, provided hereinafter) that finds the best window size to limit the searching region in the image. This algorithm should be synced with the motor parameters for insertion of needle and the ultrasound field of view and motion.

An optimization process may be set based on the physics of material and expected motion of the needle. The optimization step will define the Weights as described in Equation 3.

A summary of the tracking method is set out in Algorithm 2 (provided hereinafter).

| Algorithm 1 |
| --- |
| 1: procedure INITIAL TRACKING(First image (i = 1)) |
| 2: Generate SPs |
| 3: Manual Clicking |
| 4: Extract Features |
| 5: Set $D_{[i]}$, $G_{D_{[i]}}$ |
| 6: Initialize $KF(D_{[i]})$ |

The presented algorithm includes an initialization step for the first image which needs manual clicking by user (e.g., clinician). The variable i is image number. G is the related gray level intensity value. D is the detected needle coordinates. KF is Kalman filter. The initial tracker generates superpixels for the entire image and the user select the paws in each camera image plane.

| Algorithm 2 |
| --- |
| 1: procedure General Tracking (Frame number i) |
| 2: $[(U_i, V_i)] \leftarrow$ Predict KF |
| 3: Create sub-images based on $(U_i, V_i)$ |
| 4: Generate SPs |
| 5: for $SP_{[i]}$ do |
| 6: Extract Features (described in equation 1) |
| 7: Find SP with minimum Score |
| 8: Set $D_{[i]}$, $G_{D_{[i]}}$ |
| 9: Set Weights based on optimization step |
| 10: Set Window_Size based on adjustment step |
| 11: Update_$KF(D_{[i]})$ |

The presented algorithm includes a general tracker. The variables are defined in Algorithm 1. The variable j denotes the j-th superpixel. The general tracker uses a Kalman filter to predict the window region in the image number i based on previous images.

Device Movement Control Method

Figure 6:
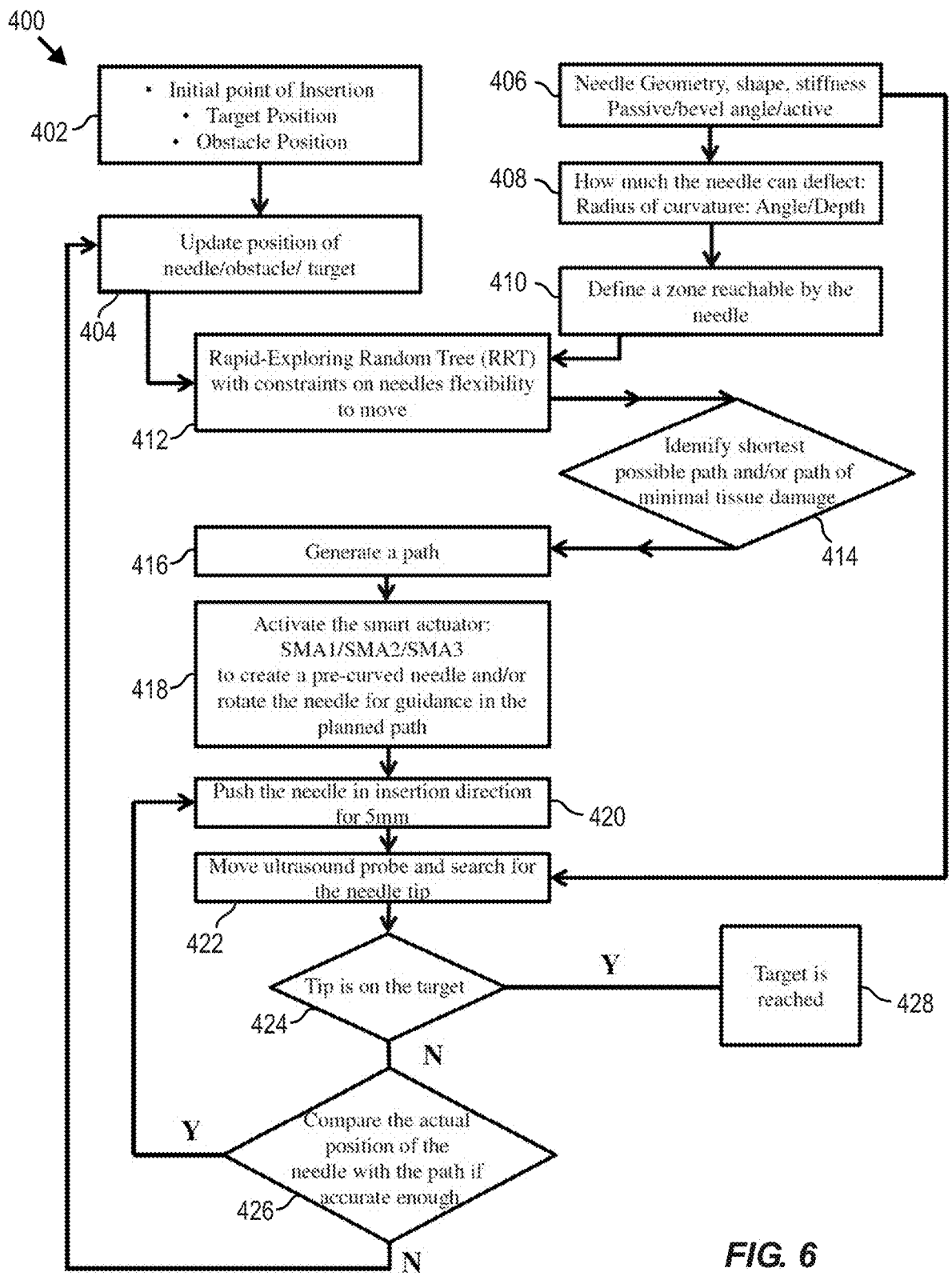
FIG. 6 is a logic diagram showing steps of a method for controlling movement of a steerable surgical device that is insertable into mammalian tissue according to one embodiment.

FIG. 6 is a logic diagram 400 showing steps of a method for controlling movement of a steerable surgical device that is insertable into mammalian tissue. Starting at upper left, at step 402, an initial point of insertion, an initial target position, and initial positions of one or more obstacles are determined (e.g., with preoperative imaging according to a surgical plan). At step 404 (which may be optional), positions of one or more of the needle, obstacles, and/or the target may be updated. At step 412, a Rapid-Exploring Random Tree (RRT) scheme is performed to generate a potential transit paths for the needle, taking into account constraints on the ability of the steerable surgical device (e.g., needle) to move, determined according to steps 406, 408, and 410. Step 406 includes defining or determining physical properties of the needle such as needle geometry, shape, and stiffness; whether the needle is passively or actively steerable; and presence of any bevel angle. Step 408, which takes into account the results of step 406, includes defining or determining the maximum deflection the needle can withstand, considering radius of curvature as well as angle and insertion depth. Step 410, which takes into account the results of step 408, includes defining or determining a zone within the tissue reachable by the needle, wherein such zone may be optionally represented as a cone or other shape. Taking into account the results of steps 404 and 410, the RRT scheme according to step 412 will identify potential paths that avoid one or more defined obstacles within, proximate to, or bounding the tissue. Such obstacles may include organ boundaries and/or other sensitive structures. From the potential paths identified in step 412, one or more desired paths are identified in step 414, with the desired path(s) preferably embodying a shortest possible path length and/or a path that minimizes damage to the tissue attributable to transit of the steerable surgical device through the tissue. In certain embodiments, the desired transit path(s) identified in step 414 exhibit at least one of the following features (i) or (ii): (i) it minimizes damage to the tissue attributable to transit of the steerable surgical device through the tissue, or (ii) it minimizes distance of transit of the steerable surgical device between the insertion point and the target point. From the desired transit path(s), a path for the steerable surgical device including a needle is generated in step 416. After the transit path is generated, smart actuators SMA1 to SMA3 are activated in step 418, such as to create a pre-curved needle, and/or to rotate the needle (using the rotary positioning motor) for guidance along at least one segment of the generated transit path (e.g., to prepare the needle to be pushed (e.g., a distance of about 5 mm) along at least one segment of the transit path). Thereafter, according to step 420, the needle is pushed (e.g., about 5 mm) in the insertion direction. According to step 422, an ultrasound probe is moved to search for the needle tip in a new location. In certain embodiments, step 422 includes moving the ultrasound probe along (e.g., parallel to) the segment of the transit path traversed by the needle (e.g., in a forward direction) and images of an interior portion of the tissue are captured until the needle is no longer visible in the captured images. Step 422 may further include moving the ultrasound probe in a reverse direction by one or more frames (e.g., at least one frame) until an image of an interior portion of the tissue showing the needle tip is captured. This will represent the updated position of the needle tip. According to step 424, a comparison is made between the needle tip position and the position of the target. If the needle tip position is at the intended target point position, then the insertion process stops according to step 428. Otherwise, if the needle tip position does not coincide with the target point position, then according to step 426 a comparison is made between the actual position of the needle and the path generated in step 416 to determine whether the path remains sufficiently accurate for further advancement of the needle to be able to reach the target position. If yes, then the needle is pushed again in the insertion direction according to step 420, and the process of locating the needle tip according to steps 422 and 422 is repeated. If no, then images captured by the probe may be used to update position of the needle (and, optionally, to update position of obstacles and/or target) according to step 404. The method then proceeds to step 412 by which RRT is used to generate an updated transit path taking into account constraints on the needle's flexibility to move and the results of step 410, then steps in the process (e.g., sequential performance of steps 414, 416, 418, 420, 422, and 424) are resumed until the target is reached (i.e., according to step 428).

Figure 7A:
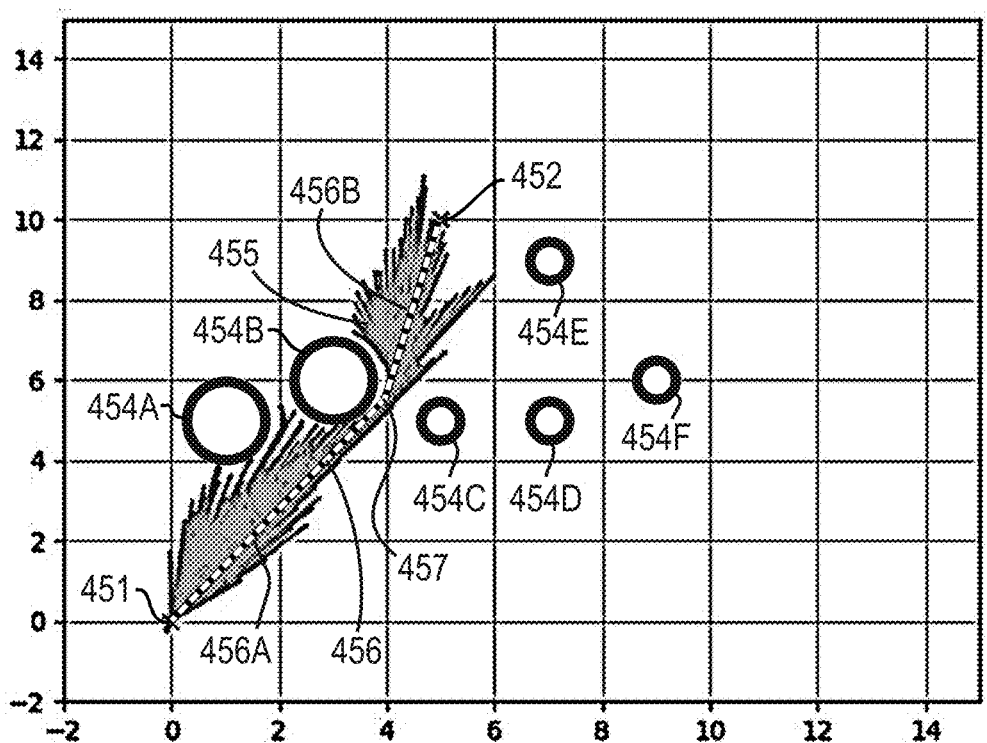
FIG. 7A illustrates positions of obstacles, potential paths, and a processor-selected path according to an implementation of a Rapid-exploring Random Tree (RRT) routing for determining an initial or updated transit path for transit of a steerable surgical device through tissue of a mammalian body.
Figure 7B:
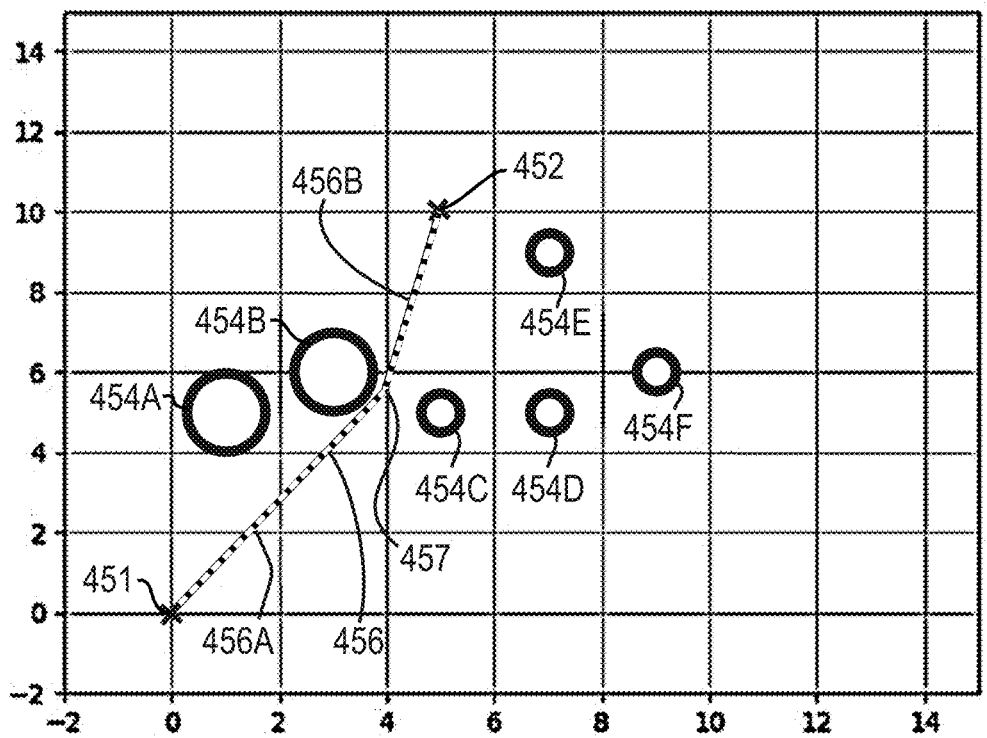
FIG. 7B is identical to FIG. 7A, except with omission of non-selected potential paths identified by a RRT routing algorithm.

Path Planning with Obstacle Avoidance for Needle Navigation:

FIGS. 7A and 7B illustrate positioning of obstacles 454A-454F and implementation of a Rapid-exploring Random Tree (RRT) routing scheme for determining an initial or updated transit path between an insertion point 451 and a target point 452. Python code was developed to implement RRT to find the best path for a needle to take to reach the target point 452 while avoiding the obstacles 454A-454F. This path planning algorithm makes a decision on the direction of a needle's bevel tip angle (governed by needle rotation), and the insertion depth at each stage of the needle insertion. The deflection of the needle in the tissue depends on the needle's properties such as its shape, bevel tip angle, its material and stiffness, as well as the properties of the tissue being used. Generally, the needle reaches the points that are located in a cone-shaped space with a limited angle, wherein any points outside of this cone cannot be reached by the needle. The angle of the cone is defined by the properties of the needle and the tissue. Additionally, the angle of this cone may change during insertion, and in most cases the angle increases while a needle is inserted deeper inside the tissue. The path planning algorithm addresses these factors to provide a path with higher accuracy. In certain embodiments, a code for 2D path planning may be used based on a constant possible angle of insertion. Referring to FIG. 7A, multiple potential paths 455 emanating from the insertion point 451 and seeking to reach the target point 452 are shown. The majority of potential paths (which are not selected) terminate when it is determined that the potential path will reach an obstacle 454A-454F and/or will not reach the target point 452. The optimum path 456 that is selected includes a first path portion 456A and a second path portion 456B with a bend or curve region 457 arranged therebetween. FIG. 7B is identical to FIG. 7A, except for omission of the non-selected potential paths 455, to clearly depict the selected path 456 between the insertion point 451 and the target point 452 with avoidance of all obstacles 454A-454F. The process of path planning is fully automated, is useable with a system disclosed herein to cause the steerable surgical device to transit through the tissue between the insertion point 451 and the target point 452 under control of at least one processor without human intervention.

Characterization of Active Needle Structure During Actuation

To validate the feasibility and measure the precision of the self-sensing electrical resistance feedback control system in path tracking control of multiple interacting SMA actuators, experiments were conducted on a prototype SMA multi-wire actuated 3D steerable active needle. The prototype was a 4:1 scaled model of 17-gauge hypodermic needle (outer diameter of 6 mm, inner diameter of 1.5 mm) fabricated of 3D printed parts, namely, a rigid base and links, and soft joints. FIG. 8A is a perspective view of the modeled active needle 500, including first through fourth tubular body members 501-504 (with the fourth body member 504 having a pointed tip), and soft elastic joints 506-508 arranged between different body members 501-504. A longitudinal alignment member 510 extends through triangular central apertures defined in the body members 501-504 and the joints 506-508, to facilitate concentric alignment of the foregoing components. Three equi-angularly distanced pairs of through-holes 511-513 extend through the body members 501-504 and the joints 506-508 to accommodate the passage of three SMA-wire actuators (not shown), which extend through lateral openings 514 in the first tubular body member 501, pass through the body members 501-504 in a generally longitudinal direction, and loop through an internal structure of the needle 500 (e.g., to reverse direction within the fourth body member 504). The configuration of the needle 500 was designed to achieve active 3D steering, with the soft elastic joints 506-508 serving to enhance flexibility of the needle 500. Actuation of three SMA-wire actuators extending through the paired through-holes 511-513 may be used to realize 3D motion at a tip 505 of the needle 500. FIG. 8B is a perspective view of one of the elastic joints 506 separate from the needle 500, showing the paired through-holes 511-513 as well as a triangular central aperture 515 extending therethrough. The soft elastic joints 506-508 are fabricated of PROTOLABS® Digital Clear/Translucent Photopolymer material having a Shore A hardness value of 60, a tensile strength of 4.5 MPa, and 170% elongation at breakage. The body members 501-504 are fabricated with Somos® PerForm polymeric material having a tensile strength of 68 MPa.

Figure 9:
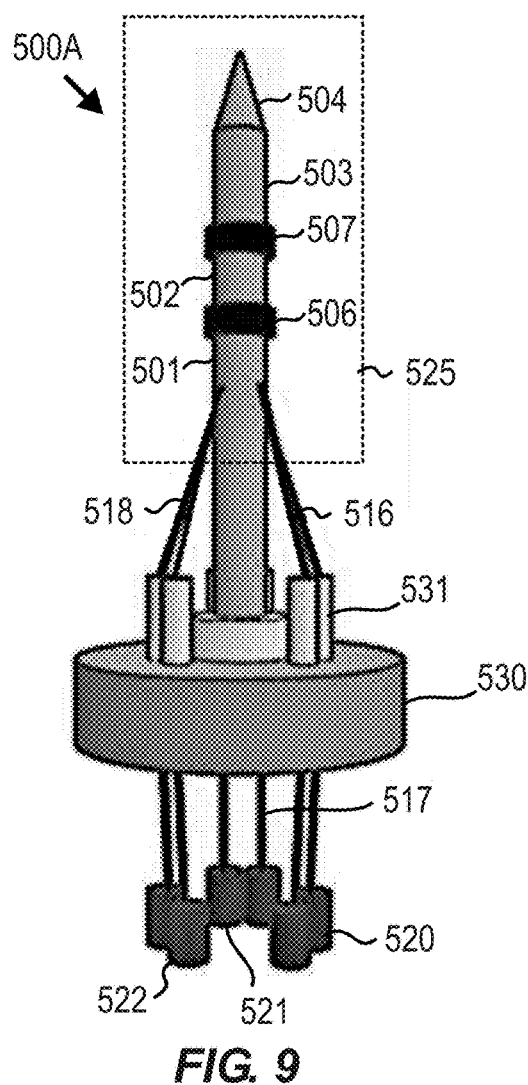
FIG. 9 is a perspective schematic view of an experimental setup for testing actuation of an active needle prototype positioned vertically in air.
Figure 10:
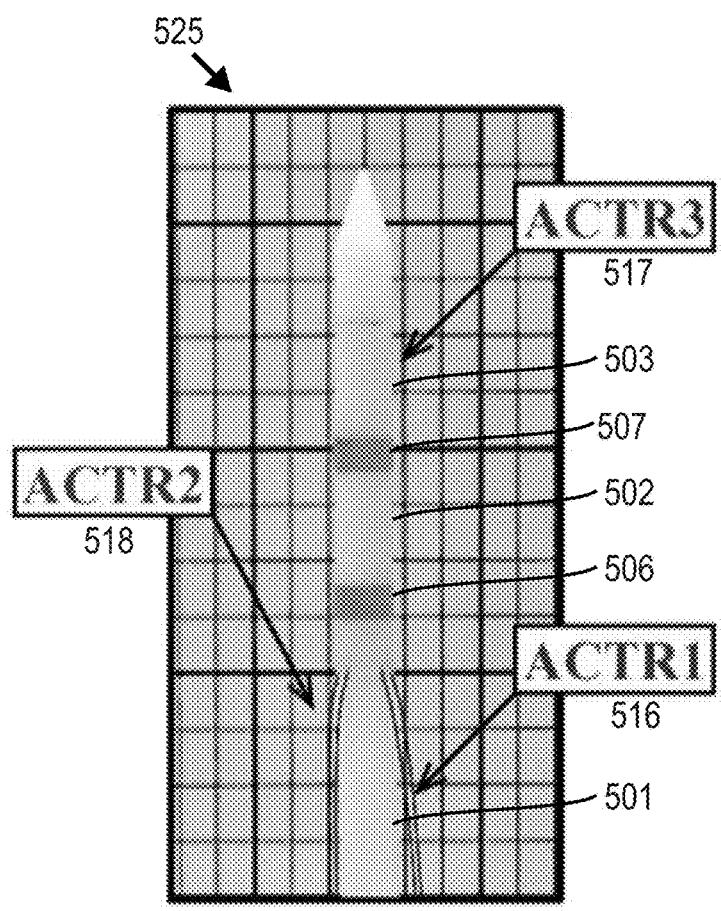
FIG. 10 is a photograph of an upper portion of the active needle prototype supported by an experimental setup according to FIG. 9.

FIG. 9 illustrates an experimental setup used for testing an active needle prototype 500A (similar to the active needle 500 of FIG. 8, but omitting the third joint 508, and only loosely connecting the fourth body member 504 without SMA actuators passing through the fourth body member 504). A first body member 501 of the needle 500A was supported by a rigid base 530 having three pairs of tubular grommets 531 extending therethrough in a vertical direction. Three SMA-wire actuators 516-518 were threaded through the needle prototype 500 and the grommets 531, and connected via pairs of electric leads 520-522 to a triple output programmable DC power supply (not shown; RIGOL DP832, RIGOL Technologies), and actuated via Joule heating. Prior to the experiment, the SMA-wire actuators 516-518 were trained with 80 cycles of heating and cooling prior. The power supply was equipped with a built-in output (voltage, and electric current) sensing module that measured the voltage and electrical current across the SMA-wire actuators 516-518 with 10 mV/10 mA measurement resolution, during actuation duty cycles. The position at the needle tip was tracked via a vision tracking program in MATLAB® software (Mathworks Inc., Natick, Mass.). The images were captured using a Canon® PowerShot SX60 HS camera with a 3.8-247.0 mm 1:3.4-6.5 USM lens at 1280× 720 30 fps, during the actuation. An upper portion 525 of the needle 500A of the illustration of FIG. 9 is shown in photographic form in FIG. 10, in which the SMA-wire actuators 516, 517, and 518 bear additional labels ("ACTR1"), ("ACTR2"), and ("ACTR3"), respectively, to correspond to various figures that follow.

Figure 11A:
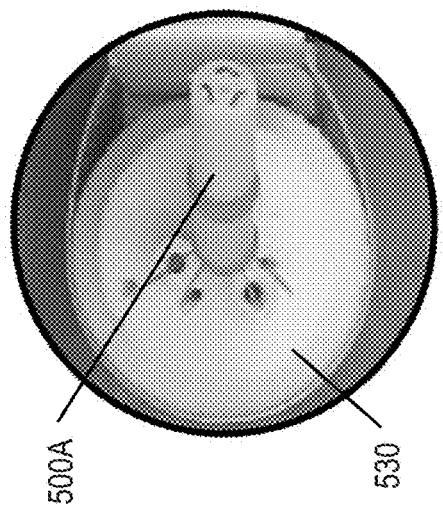
FIGS. 11A and 11B provide top and front views, respectively, of an active needle prototype supported in the experimental setup according to FIG. 9, with deflection of the needle due to actuation of a first SMA-wire actuator.
Figure 12A:
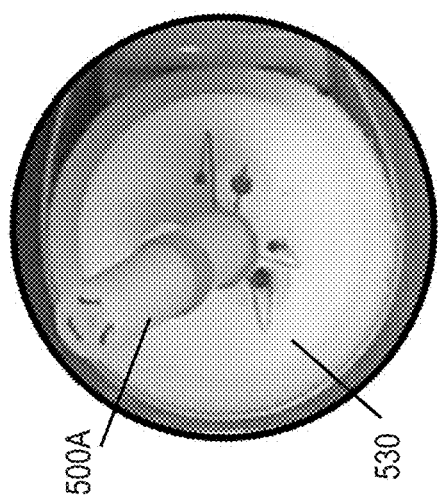
FIGS. 12A and 12B provide top and front views, respectively, of the active needle prototype supported in the experimental setup according to FIG. 9, with deflection of the needle due to actuation of a second SMA-wire actuator.
Figure 13A:
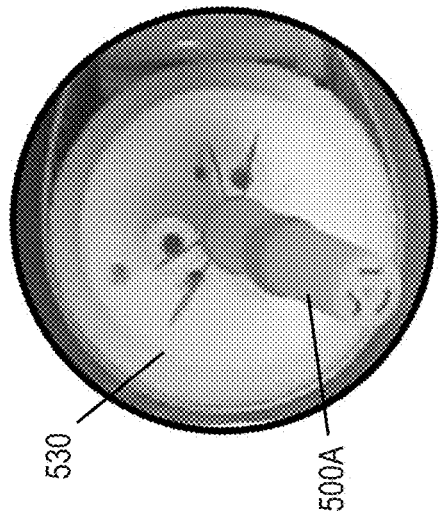
FIGS. 13A and 13B provide top and front views, respectively, of the active needle prototype supported in the experimental setup according to FIG. 9, with deflection of the needle due to actuation of a third SMA-wire actuator.
Figure 11B:
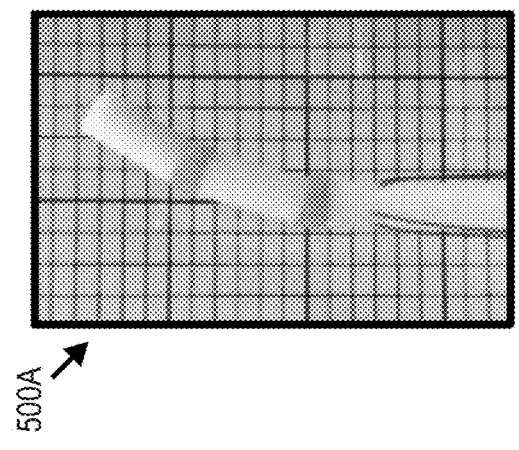
Figure 12B:
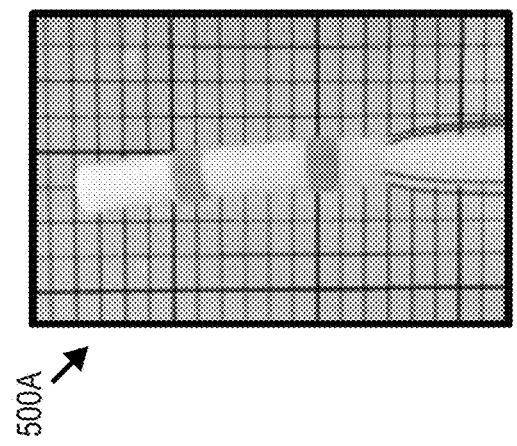
Figure 13B:
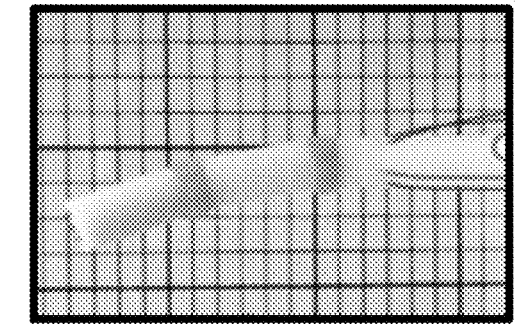

In a first set of characterization experiments, mechanical characteristics of the flexible structure of an active needle was tested in single SMA-wire actuation duties where each of the three SMA-wire actuators 516 (ACTR1), 517 (ACTR2), and 518 (ACRT3) were actuated separately. The induced strain in the SMA-wire actuators impels the flexible structure of an active needle to deflect, causing a displacement in position at the needle tip. FIGS. 11A and 11B provide top and front views, respectively, of the needle 500A supported by the rigid base 530 with deflection of the needle due to actuation of a first SMA-wire actuator 516 (ACTR1). Similarly, FIGS. 12A and 12B provide top and front views, respectively, of deflection of the needle 500A due to actuation of a second SMA-wire actuator 517 (ACTR2), and FIGS. 13A and 13B provide top and front views, respectively, of deflection of the needle 500A due to actuation of a second SMA-wire actuator 518 (ACTR3), with the needle 500A supported by the rigid base 530.

Figure 14C:
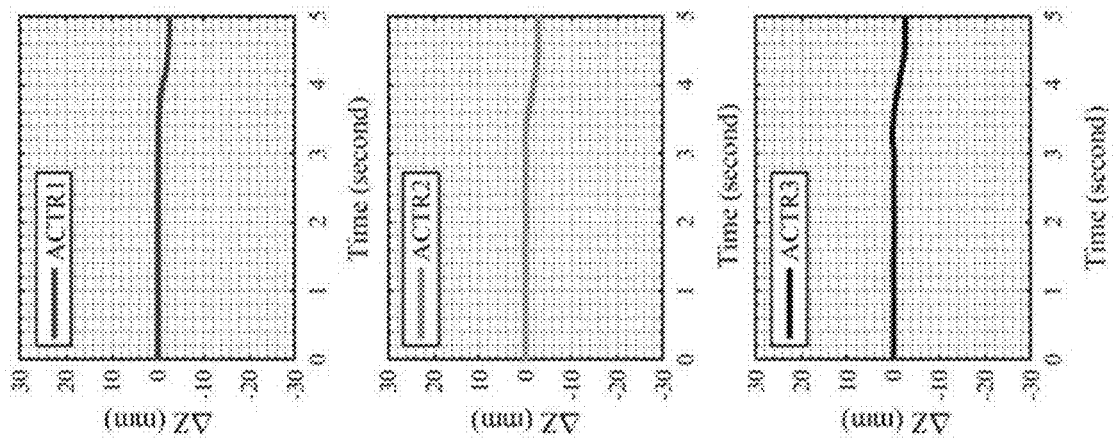
FIGS. 14A-14C provide plots of change in X-, Y-, and Z-position versus time, respectively, during the actuation of one of three SMA-wire actuators under single actuation duty cycles (i.e., individual actuation of SMA-wire actuators ACTR1, ACTR2, ACTR3) for the active needle prototype supported in the experimental setup according to FIG. 9.
Figure 14B:
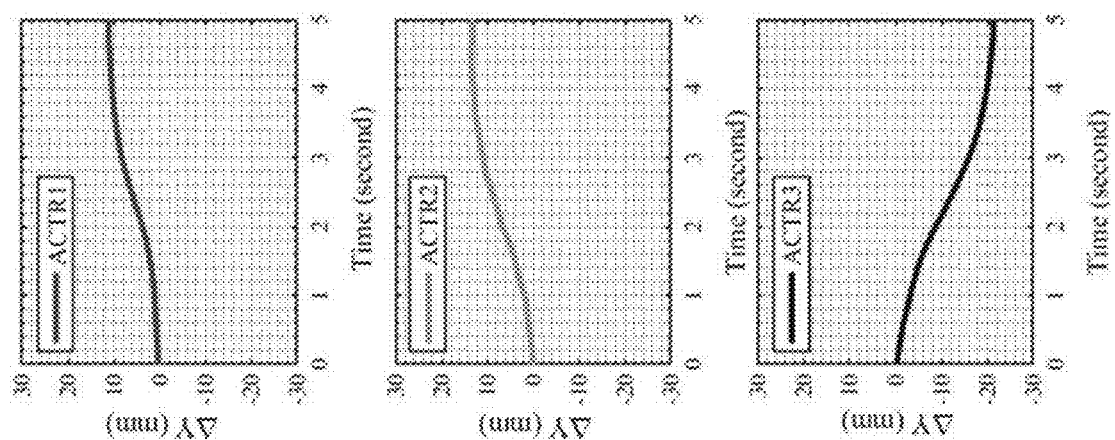
Figure 14A:
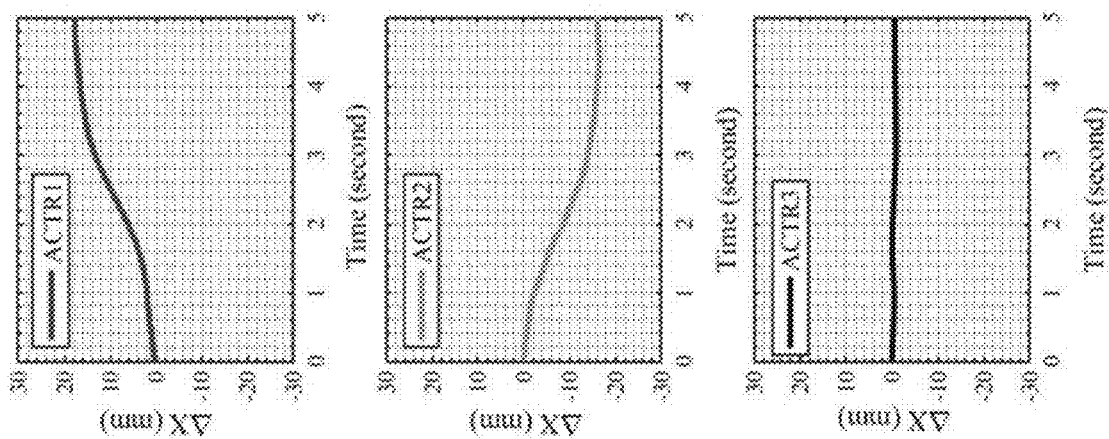

Position of the active needle at the needle tip was tracked in three-dimensional (3D) space (X,Y,Z) during the actuation of the three SMA-wire actuators 516 (ACTR1), 517 (ACTR2), and 518 (ACRT3) under single actuation duty cycles, using a computer vision-based position tracking method. Results are illustrated in FIGS. 14A-14C. The three frames of FIG. 14A provide ΔX values (in millimeters) as a function of time for the three SMA-wire actuators 516

(ACTR1), 517 (ACTR2), and 518 (ACRT3), respectively. Similarly, the three frames of FIG. 14B provide ΔY values (in millimeters) as a function of time for the three SMA-wire actuators 516 (ACTR1), 517 (ACTR2), and 518 (ACRT3), respectively. Likewise, the three frames of FIG. 14C provide ΔZ values (in millimeters) as a function of time for the three SMA-wire actuators 516 (ACTR1), 517 (ACTR2), and 518 (ACRT3), respectively, wherein it is noted that the change in the Z dimension was very small for each case since the needle 500A was constrained from below due to support by the rigid base 530 shown in FIGS. 9, 11A, 12A, and 13A.

Figures 15A, 15B, 15C:
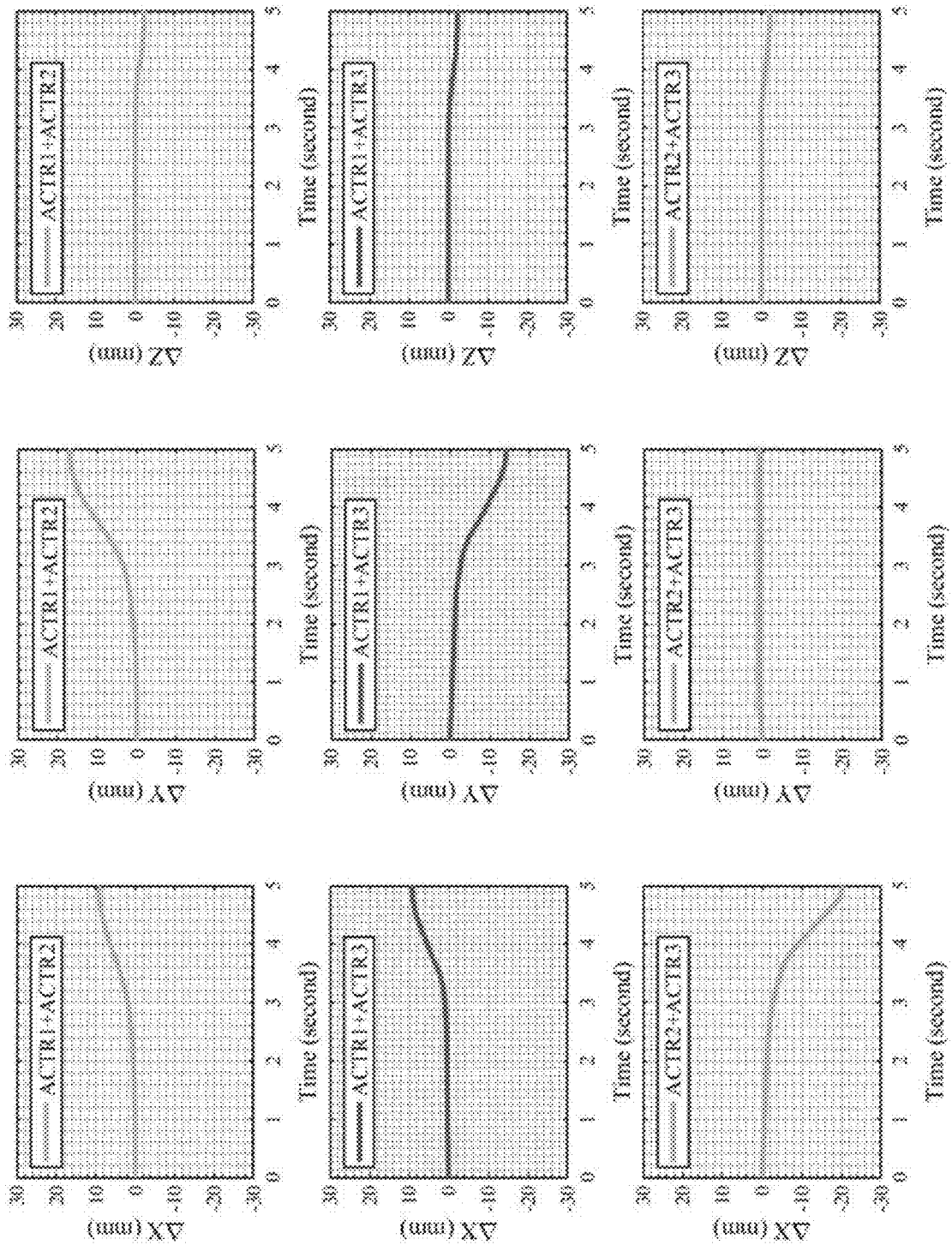
FIGS. 15A-15C provide plots of change in X-, Y-, and Z-position versus time, respectively, during the actuation of two of three SMA-wire actuators under dual SMA-wire actuator duty cycles (i.e., involving simultaneously actuation of different pairs of SMA-wire actuators ACTR1, ACTR2, ACTR3) for the active needle prototype supported in the experimental setup according to FIG. 9.

In addition to single actuation schemes, multi-actuation schemes in which multiple actuators were actuated in parallel, were implemented to actuate three interacting SMA-wire actuators to manipulate the active needle. In this set of characterization experiments, mechanical characteristics of the flexible structure of the active needle was tested under dual SMA-wire actuation duties each involving synchronous actuation of different pairs of the three SMA-wire actuators 516 (ACTR1), 517 (ACTR2), and 518 (ACTR3). Position at the needle tip was tracked in 3D space (X,Y,Z) during the actuation. Results are illustrated in FIGS. 15A-15C. The three frames of FIG. 15A provide ΔX values (in millimeters) as a function of time for three different pairings of SMA-wire actuators (i.e., 516 (ACTR1)+517 (ACTR2); 516 (ACTR1)+518 (ACTR3); and 517 (ACTR2)+518 (ACTR3), respectively). Similarly, the three frames of FIG. 15B provide ΔY values (in millimeters) as a function of time for the three different pairings of SMA-wire actuators (i.e., 516 (ACTR1)+517 (ACTR2); 516 (ACTR1)+518 (ACTR3); and 517 (ACTR2)+518 (ACTR3), respectively). Likewise, the three frames of FIG. 15C provide ΔZ values (in millimeters) as a function of time for three different pairings of SMA-wire actuators (i.e., 516 (ACTR1)+517 (ACTR2); 516 (ACTR1)+518 (ACTR3); and 517 (ACTR2)+518 (ACTR3), respectively), wherein the change in the Z dimension was very small for each case.

The dual actuation scheme unlocks additional set of points in 3D space that are within reach of the needle tip, leading to an increased workspace volume of the active needle.

SMA-Wire Actuator Characterization

Characterization of SMA-wires in terms of actuator strain and electrical resistance is an important step in exploiting self-sensing characteristics and sensor functionality of SMA actuators. Electrical resistance of an SMA wire depends on the fraction concentration of the present phases, i.e., austenite and martensite, in the material, and changes measurably during the phase transformation. In addition, the strain in an SMA-wire actuator is a function of the volume fraction concentration for the martensite and austenite phases present in the material during the phase transformation. Consequently, the strain and the electrical resistance in an SMA-wire are correlated. The strain-resistance correlation in the SMA wires conveys their unique self-sensing capabilities and provides the scope for a sensor-less control system adopting the SMA-wire actuator as position sensors by measuring their electrical resistance. The strain-resistance correlation, obtained from characterization experiments, was applied to develop mapping functions that relate the system output (i.e., position of the end effector) to the temperature-induced strain in SMA-wire actuator and its electrical resistance at different actuation levels. Characterizing the response of SMA-wire actuators and their correlated strain-resistance behavior contributes to constructing system models and designing control systems with internal resistance feedback to control SMA-wire actuators.

To characterize the response and quantify the strain-resistance correlated behavior of SMA-wire actuator, the electric current and voltage across the SMA-wire actuator was measured during the actuation, and the electrical resistance of the SMA wire is calculated using Ohm's law. The thermodynamic equilibrium defines the temperature of an SMA wire, in the course of Joule heating actuation, as a function of the input electrical power, heat conduction between the martensite phase at a low temperature and a phase at a higher temperature (martensite or austenite) due to the latent heat of phase transformation, and the heat convection to the ambient environment. It is recognized that the input electrical power directly impacts the temperature of the SMA wire; accordingly, the strain-resistance response of the SMA wire was characterized in terms of the electrical power input to the system.

Figure 16A:
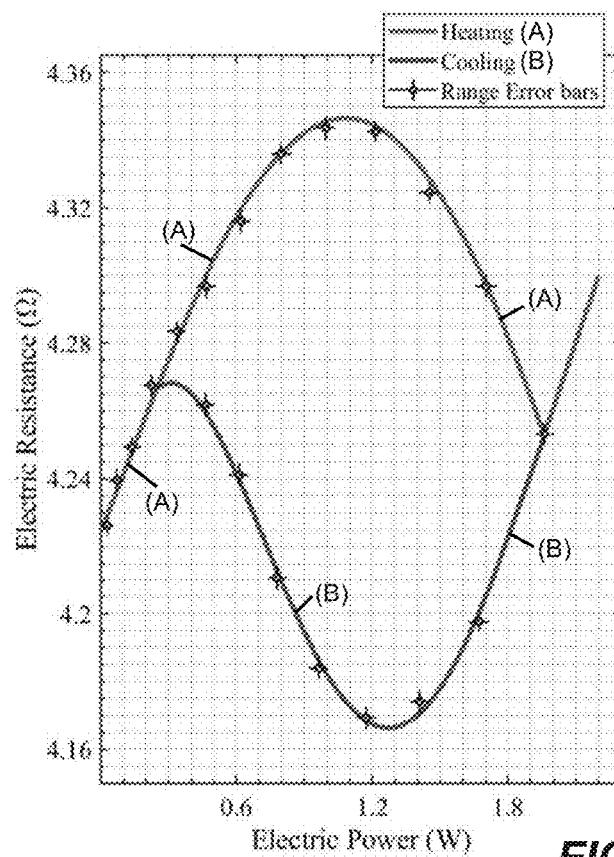
FIGS. 16A-16C provide plots of measured characteristics for a first SMA wire (ACTR1) for both heating and cooling cycles, with FIG. 16A plotting electric resistance versus electric power, FIG. 16B plotting deflection versus electric resistance, and FIG. 16C plotting deflection versus electric resistance.
Figure 16B:
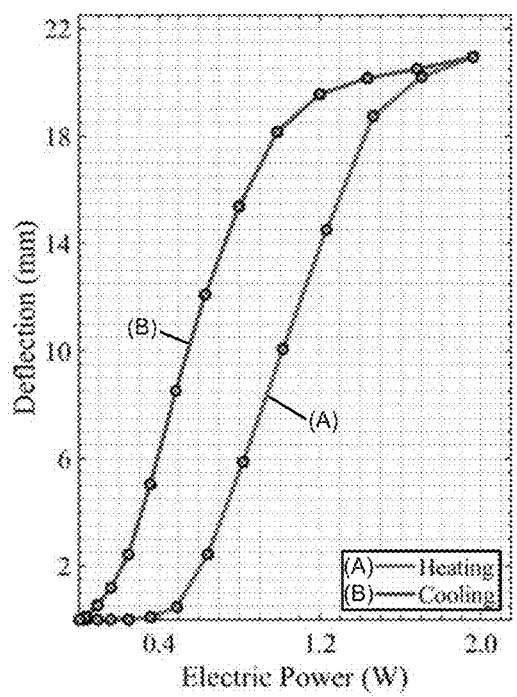
Figure 16C:
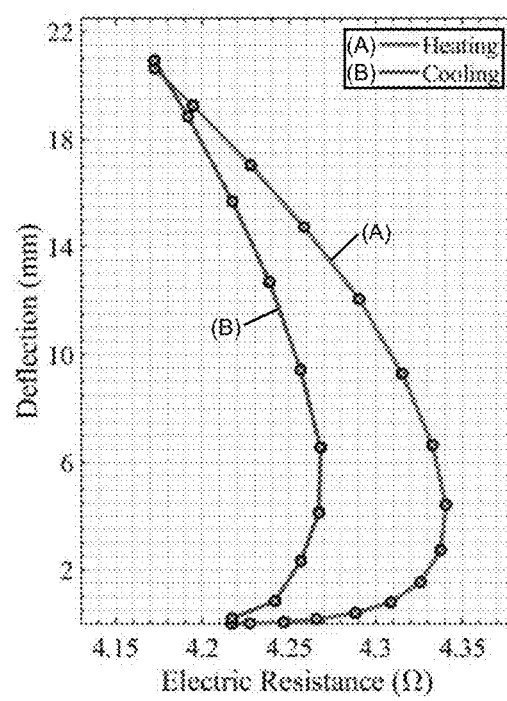

FIGS. 16A-16C provide plots of measured characteristics for a first SMA wire (ACTR1) for both heating and cooling cycles. In particular, FIG. 16A is a plot of electric resistance (Ohms) versus electric power (Watts); FIG. 16B is a plot of deflection (mm) versus electric power (Watts), and FIG. 16C is a plot of deflection (mm) versus electric resistance (Ohms) for ACTR1. Similar plots were generated for second and third SMA wires (ACTR2 and ACRT3) but are omitted from the present disclosure for brevity.

Tracking Control of 3D Steerable Active Needle with Three SMA Actuators

Figure 17B:
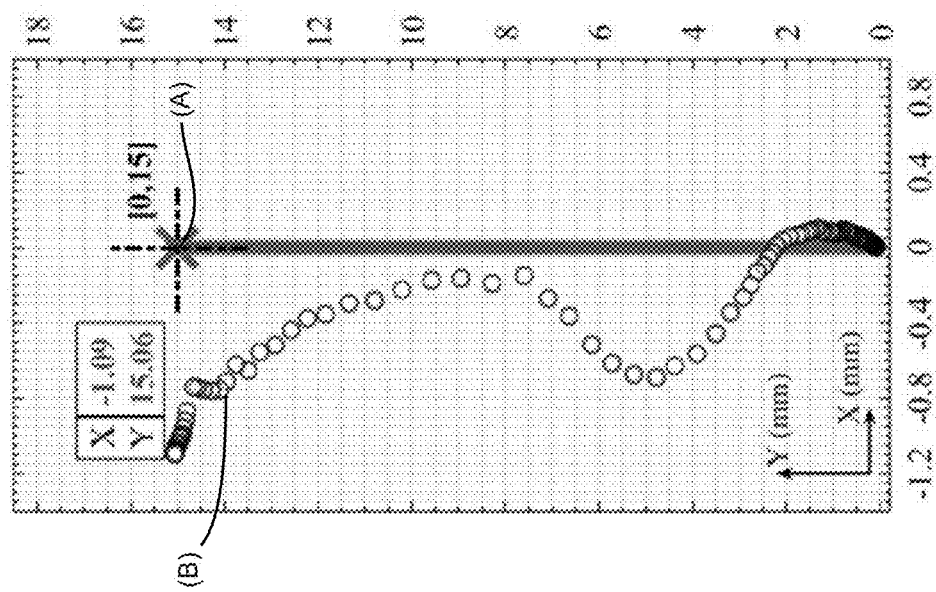
FIG. 17B is a magnified view of a portion of FIG. 17A.
Figure 17A:
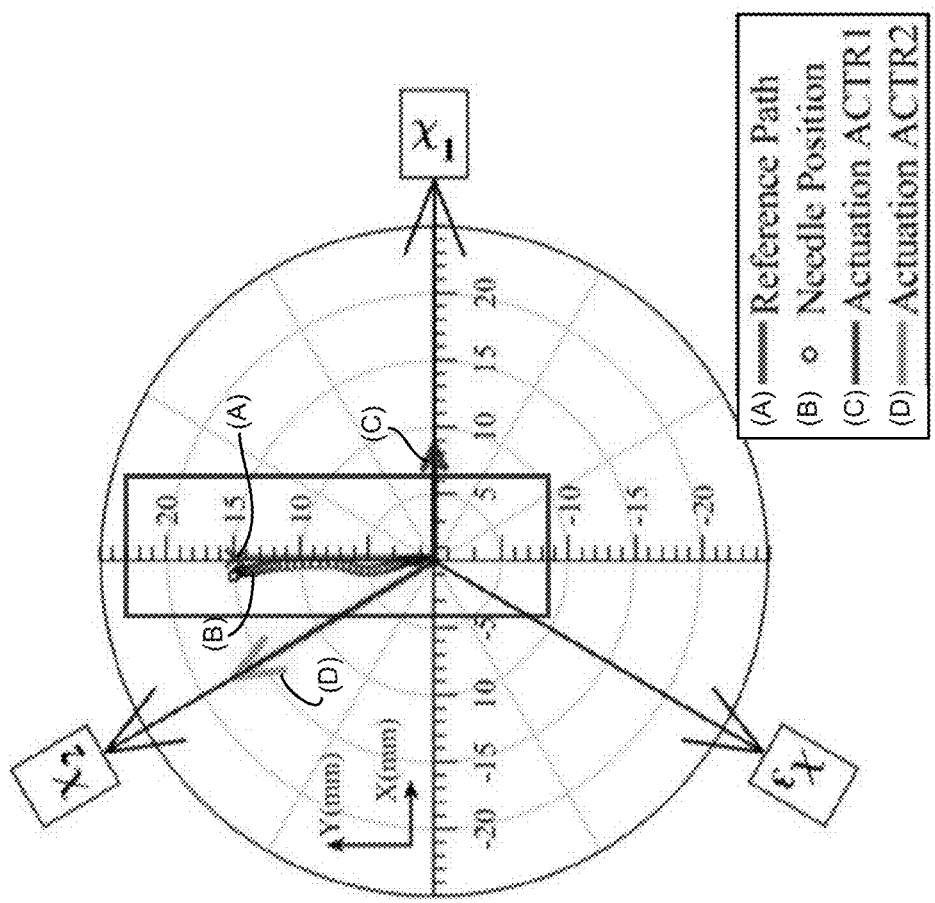
FIG. 17A is a plot of actuation duties for first and second SMA-wire actuators of an active needle in a non-orthogonal three-axis coordinate system (corresponding to actuation axes of three SMA-wire actuators), with a superimposed travel path of a needle tip and a reference path both being plotted in x,y coordinates.

A control scheme was implemented on a triple set of interacting SMA-wire actuators to control the active needle. Manipulating the active needle tip to track a desired path required controlled actuation of three interacting SMA-wire actuators. The performance of a self-sensing electric resistance feedback control system as disclosed herein in manipulating the needle tip for path tracking was tested and the results are presented in FIGS. 17A and 17B. As shown by the vectors (C) and (D) along axis $X_1$ and $X_2$, respectively, actuation signals were provided to first and second SMA-wire actuators ACTR1 and ACTR2. The reference path (A) was a vertical path (i.e., along the Y-axis in the Cartesian coordinate system) with the start point $P_1$ (0,0), and the end point $P_2$ (0,15), with units in millimeters. The tracked needle position (B) (measuring position at the needle tip) relative to the reference path is shown in FIG. 17A, with a magnified view thereof shown in FIG. 17B. As shown in FIG. 17B, actuation of the first and second SMA-wire actuators ACTR1 and ACTR2 caused the needle tip to be positioned close to the reference path (A), with the final position of the needle tip being at (Cartesian) X,Y coordinates of (−1.09, 15.06), being reasonably close to the target endpoint of (0, 15). A multitude of positional data points for needle position (B) are shown in FIG. 17B.

The preceding experiments demonstrated controlled manipulation of a 3D steerable active needle for surgical procedures via actuation of multiple interacting SMA-wire actuators. Developing an active needle that responds accurately to SMA actuation is a challenging task due to the complex electromechanical behavior of SMA materials, with such behavior being nonlinear, characterized by hysteresis, and history dependent.

Evaluation of Performance of Active Needle Inside Phantom Tissue

Figure 18:
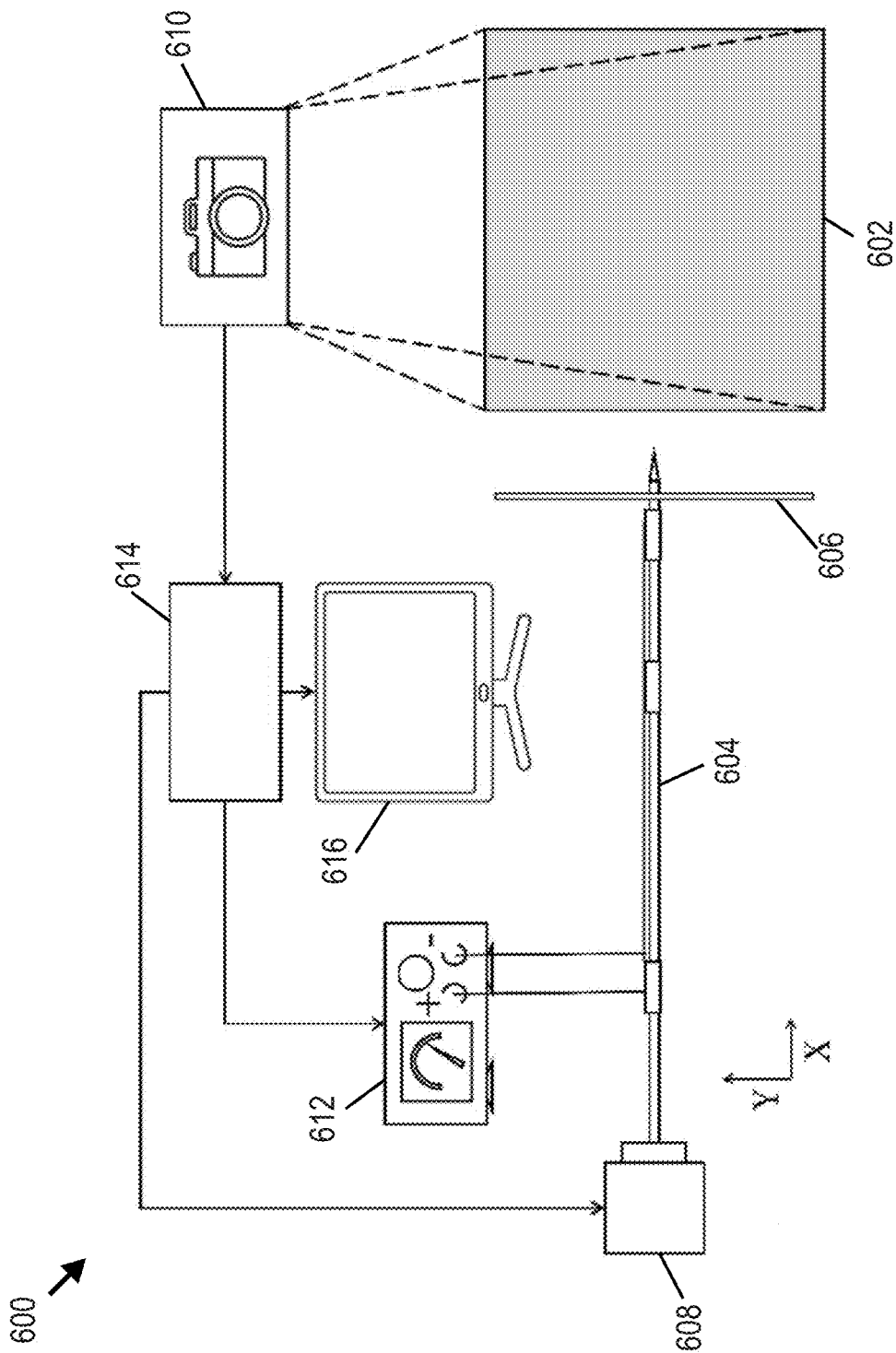
FIG. 18 is a schematic view illustration of an experimental setup used for inserting a needle into tissue-mimicking phantom material for evaluating performance of an active needle.

The behavior of an active needle including a single active SMA-wire actuator in tissue-mimicking phantom material was assessed. The experimental setup shown in FIG. 18 was used for needle insertion and for evaluating needle performance. A Plastisol (M-F Manufacturing Co., Ft. Worth, Tex., USA) tissue-mimicking material was used with a 3:1 ratio of plastic (polyvinylchloride suspension) to softener to form a tissue phantom 602. An active needle 604 was inserted through a guide block 606 into the tissue phantom 602 at a constant speed of 10 mm/s using a linear motorized stage 608 having 6 μm resolution. Pictures were taken with a camera 610 positioned above a test bed containing the tissue phantom 602 to measure overall deflection of the active needle 604. ImageJ software was used for video and image processing and measuring the needle deflection. In the phantom material 602, the needle was first inserted (without actuation) to a depth of 50 mm, until the actuator (i.e., the shape memory actuator (SMA) wire) was positioned completely inside the phantom material 602. At this point, a constant current (1.2 A) was supplied to the SMA wire by a power supply 612, and then the actuated needle 604 was further inserted for another 100 mm with the supply of current maintained to the SMA wire. The amount of current (1.2 A) required to actuate the SMA wire inside the phantom material 602 was higher than the current (0.7 A) required for actuation in air, because of the heat loss from the SMA wire to the surrounding phantom material 602. Both the linear motorized stage 608 and the power supply 612 were operating by the commands and signals provided by code operated with a Raspberry Pi computing device 614 having a corresponding display 616. The experiment showed that the amount of actuation force provided by a SMA wire associated with the active needle 604 is sufficiently high to bend the active needle 604 inside the tissue 602 and realize a curved path.

Figure 19A:
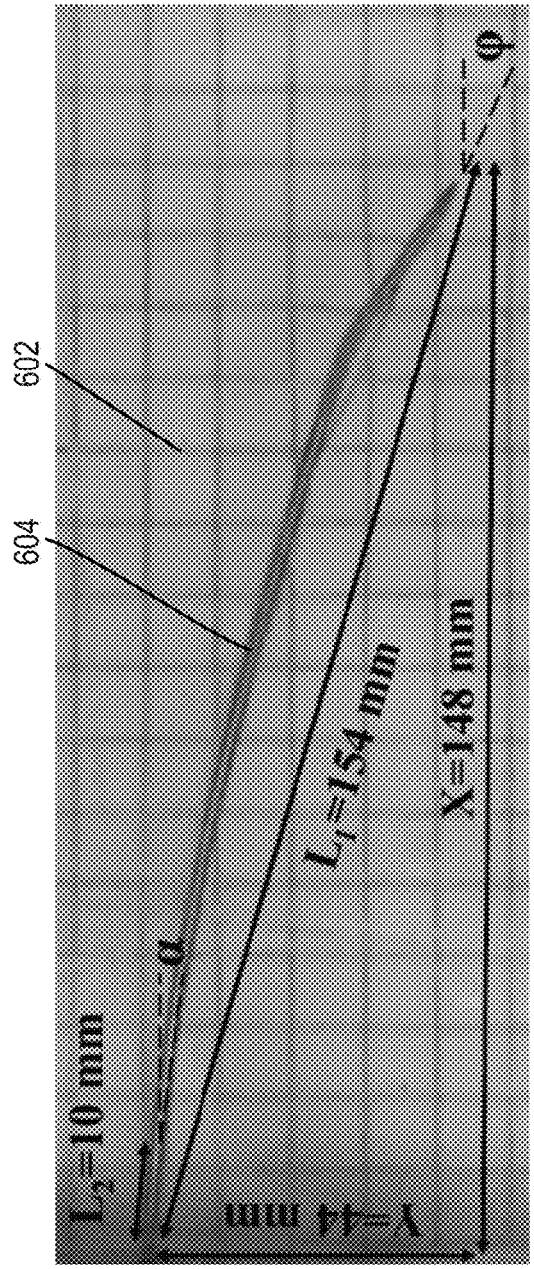
FIG. 19A is a photograph showing final deflection of an active needle inside tissue-mimicking phantom material after insertion to an axial insertion depth of 150 mm, with superimposed markings of measured dimensions and angles to be quantified.
Figure 19B:
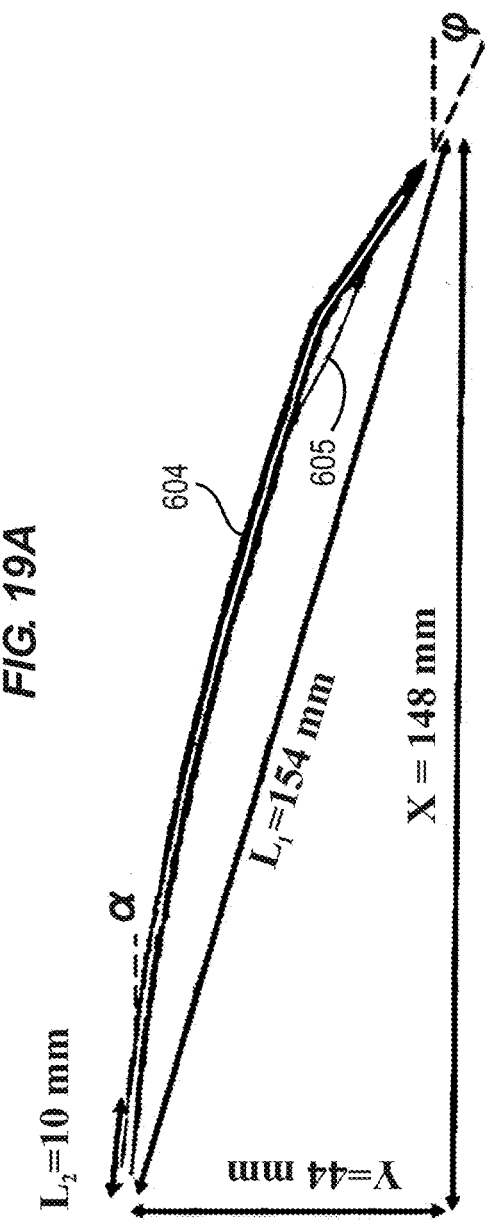
FIG. 19B is a black and white illustration of the active needle and markings of FIG. 19A, with removal of the background to promote clarity.

FIG. 19A is a photograph showing final deflection of the active needle 604 inside the phantom material 602 after insertion to an axial insertion depth of 150 mm, with superimposed markings of measured dimensions and angles to be quantified. FIG. 19B is a black and white illustration of the active needle 602 and markings of FIG. 19A, with removal of the background to promote clarity, but with addition of a label to the SMA wire 605. The angular deflection was proportional to the amount of current provided to the SMA wire. The radius of curvature was calculated for the deflected shape of the active needle.

Figure 20:
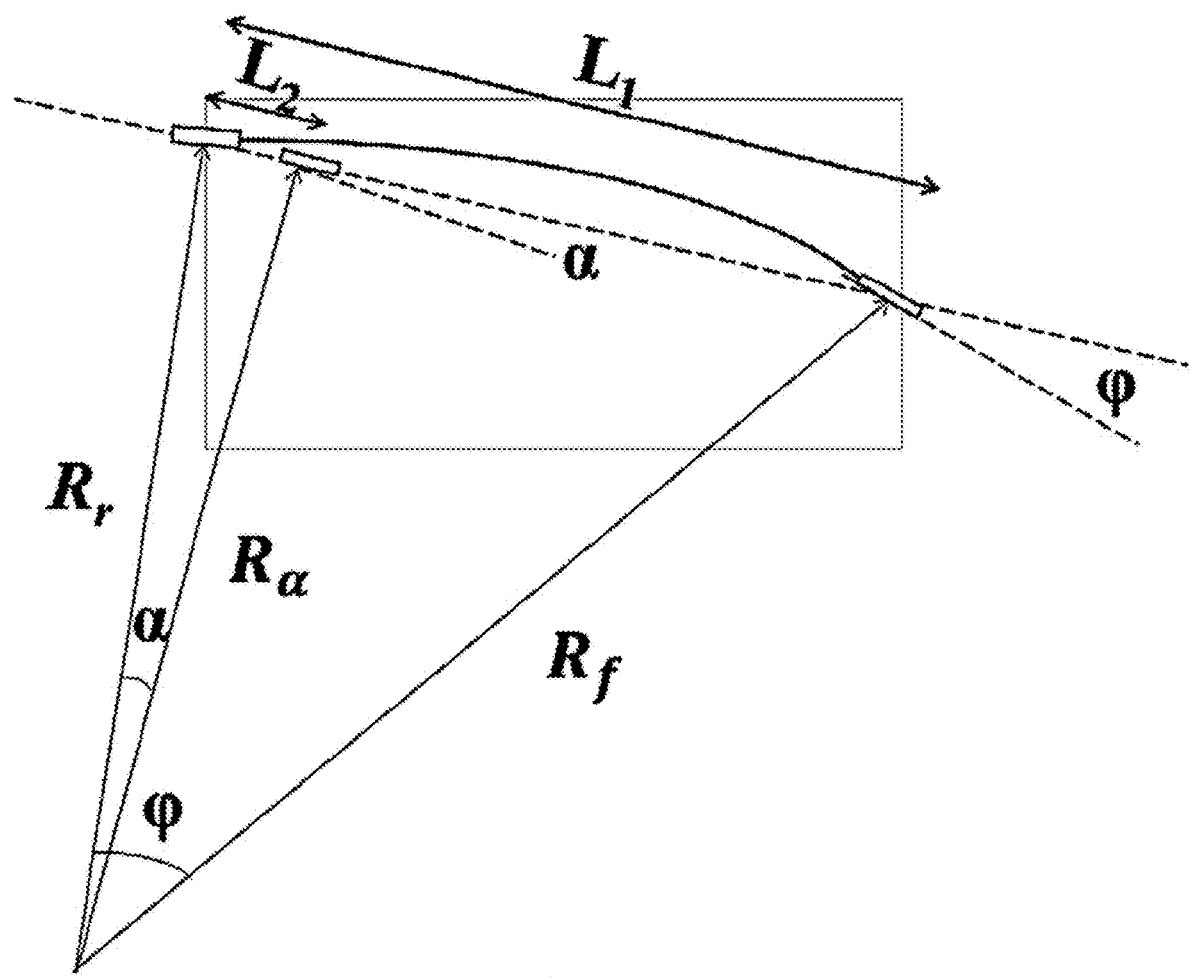
FIG. 20 is a diagram showing geometric relationships among measured lengths and corresponding angles of the active needle after an axial insertion depth of 150 mm into phantom material.

FIG. 20 is a diagram showing geometric relationships among measured lengths and corresponding angles of the active needle after an axial insertion depth of 150 mm into phantom material. From the geometric considerations shown in FIG. 20, one may approximate $R_r$ (rear radius of curvature) $R_f$ (front radius of curvature)$\approx R_\alpha$ (needle tip radius of curvature)$\approx R$, assuming that $L_1 \ll R$ and $L_2 \ll R$.

The radius of curvature of the needle is related to $\varphi$ and $L_1$ according to:

$$R = L_1/\tan(\varphi)$$

The values for $\varphi$ and $L_1$ are shown in FIGS. 20A and 20B. The angle $\alpha$ can be determined as:

$$\tan(\alpha) = (L_1/L_2)*\tan(\varphi)$$

and the resulting radius of curvature at $L_2$ is determined by:

$$R_\alpha \approx R = \frac{L_2}{\sin(\alpha)} = \sqrt{L_2^2 + (L_1/\tan(\varphi))^2}$$

Substituting the values into above equations will result in the radius of curvature of 519 mm at the needle tip, calculated as follows:

$$R_\alpha \approx R = \sqrt{10^2 + (154/\tan(16.5))^2} = 519 \text{ mm}$$

Figure 21A:
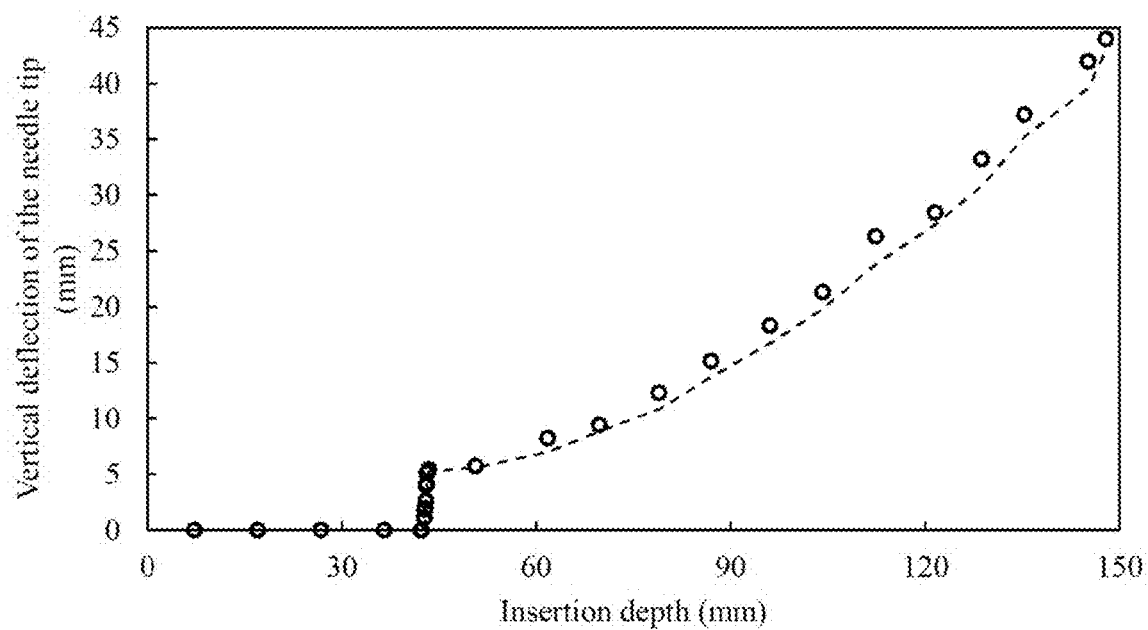
FIG. 21A is a plot of vertical deflection of an active needle tip in phantom tissue during active insertion versus depth.

FIG. 21A is a plot of vertical deflection (i.e., vertical position) of the active needle tip in phantom tissue during active insertion versus depth. For the first 42 mm, the active needle was pushed straight into the phantom material with no actuation, and thereby no vertical deflection. At this point, when the bending section of the active needle was completely located inside the phantom, the SMA wire was activated via Joule heating (providing 1.2 A of current) to realize a vertical movement of about 5.1 mm at the needle tip inside the phantom. The active needle was then pushed for another 108 mm to the final axial depth of 150 mm. The main difference between active steering and needle curving with bevel-tip needles can be seen in FIG. 21A at 42 mm of insertion depth. Upon actuation of SMA wire at this depth, the needle tip realized about 5.1 mm of vertical movement, which is not possible via needle curving with bevel-tip needles.

Figure 21B:
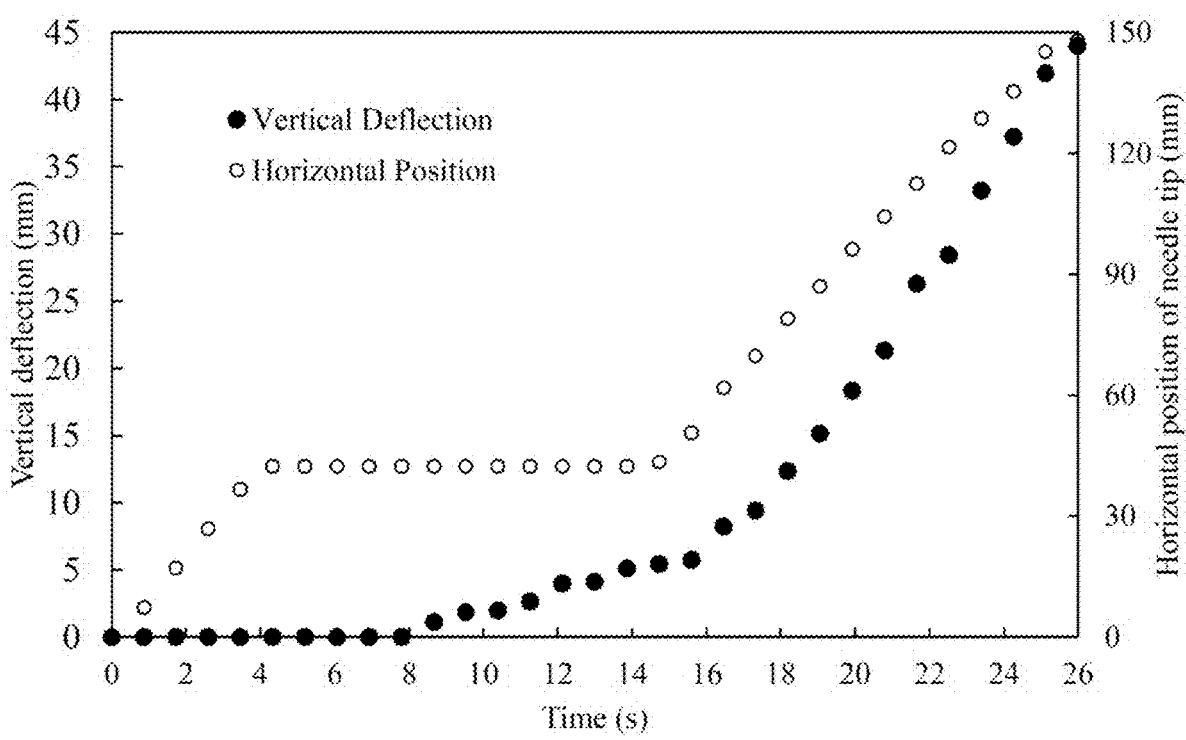
FIG. 21B provides superimposed plots of vertical deflection and horizontal position of a tip of an active needle versus time.

FIG. 21B provides superimposed plots of vertical deflection and horizontal position of a tip of an active needle versus time during insertion into phantom material. The needle was inserted into the phantom material with no actuation for the first 8 seconds, thereby following a straight path (i.e., no vertical movement). Then, the SMA wire was actuated with 1.2 A for 6 seconds (between 8 and 14 seconds) to realize vertical movement of 5.1 mm inside the phantom material. The active needle was inserted for another 12 seconds to the depth of 150 mm to realize a final vertical and horizontal movement of 44 and 148 mm, respectively at the needle tip.

Needle Insertion Visualization Using Ultrasound Machine

A tissue-mimicking phantom material was produced by pouring 1000 mm Plastisol (M-F Manufacturing Company, Haltom City, Tex.) liquid plastic (polyvinylchloride suspension) base and 330 mm plastic softener (M-F Mfg. Co.) into a small aluminum pan, stirring for a period of 45 minutes, heating in a vacuum oven to a temperature of 428° F. to bring all bubbles to the surface of the liquid, followed by removal of the top layer of liquid, then cooling and maintaining the product at room temperature for 24 hours. The resulting phantom was substantially free of bubbles.

A Digital Color Doppler Ultrasound CHISON ECO5 machine (Chison USA Inc., Bellevue, Wash.) was used in brightness mode (B-mode, permitting visualization of tissue as a two-dimensional image), with a frame per second (FPS) setting of 79, a gain setting of 90 (within a range of 0-255), a PWR setting of 15 (corresponding to pulsed wave Doppler, combinable with B-mode for examinations), a frequency of 10 MHz for collected images from testing, a dynamic (DN) contrast resolution adjustment value of 74, and a depth of influence setting of 3.7 cm.

With the ultrasound settings properly tuned, the position of a needle inserted into the phantom material was tracked. Needle tracking was accomplished via a Python code through an automated process of displaying images of the ultrasound machine and storing them on a computer as a video file, in additional to separately capturing and saving each image frame. About 400 frames were captured during needle transit through the phantom material.

A method based on iterative clustering to form superpixels was used to track the needle trajectory. As described previously herein, superpixels contract and group uniform pixels in an image, with one desirable superpixel formation method being Simple Linear Iterative Clustering (SLIC).

Figure 22A:
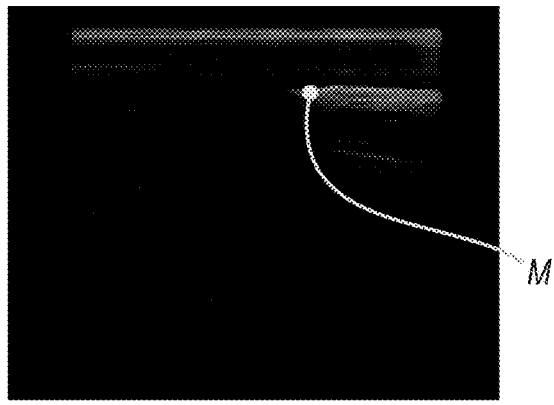
FIGS. 22A-22C are images with superimposed markers representing a tip of a needle tracked by SLIC superpixel generation using ultrasound detection of an active needle in tissue-mimicking phantom material.
Figure 23A:
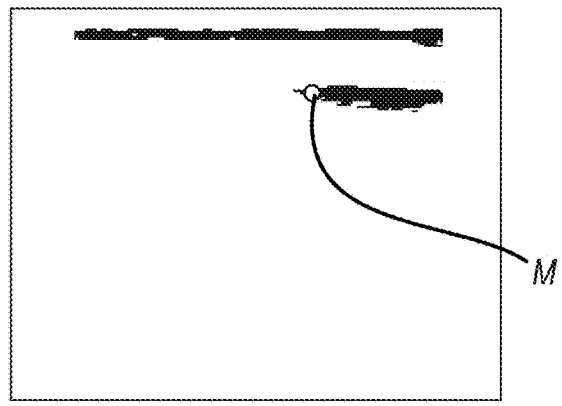
FIGS. 23A-23C are color-inverted representations of the images of FIGS. 22A-22C.
Figure 22B:
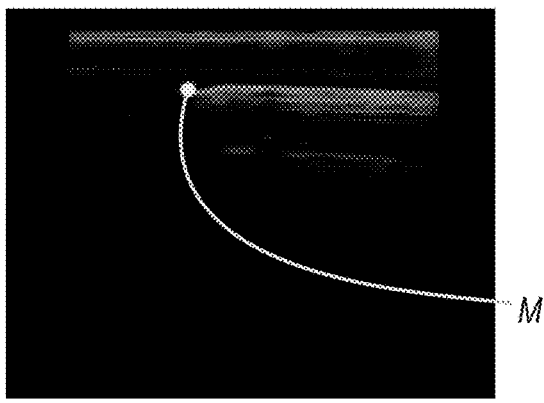
Figure 23B:
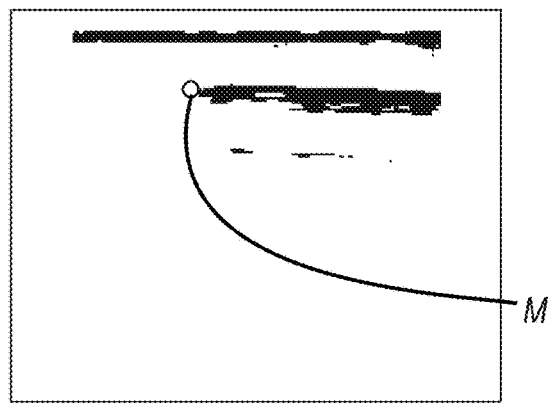
Figure 22C:
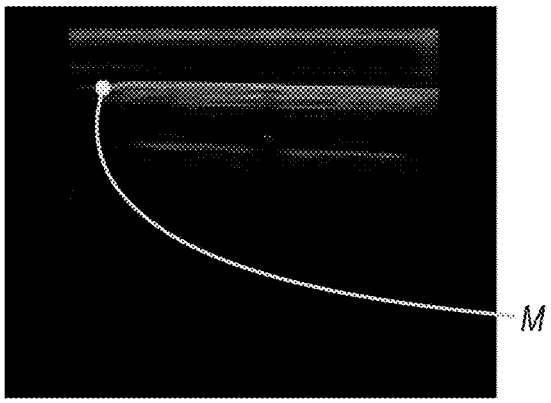
Figure 23C:
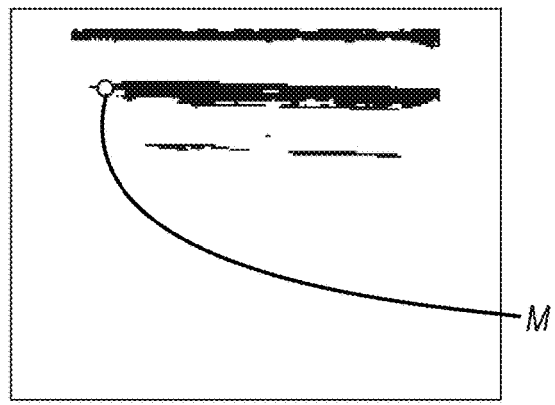

FIGS. 22A-22C are images with superimposed markers representing a tip of a needle tracked by SLIC superpixel generation using ultrasound detection of an active needle in tissue-mimicking phantom material. FIGS. 23A-23C are color-inverted representations of the images of FIGS. 22A-22C. In FIGS. 22A-22C and FIGS. 23A-23C, the marker M represents a tip of the needle tracked by SLIC superpixel generation, followed by application of a 2D Kalman filter to predict the needle tip location based on its previously tracked frames. FIGS. 22B-22C and FIGS. 23B-23C, show the needle having advanced in a direction from right to left. Needle position was successfully determined in each of the about 400 captured frames, without loss of needle tip position in any frame. This demonstrated successful and reliable detection of needle tip position within tissue using ultrasound.

In comparison with computed tomography (CT) scanning, magnetic resonance imaging (MRI), and X-ray imaging, ultrasound guidance is more appropriate to track needle trajectory for surgical procedures because it provides a real-time imaging modality. In addition, it does not involve the use of ionizing radiation, thereby avoiding exposing patients to radiation and making it applicable for intra-operative and intra-procedural image-guided procedures for clinicians.

Those skilled in the art will recognize improvements and modifications to the preferred embodiments of the present disclosure. All such improvements and modifications are considered within the scope of the concepts disclosed herein and the claims that follow.

The invention claimed is:

1. A system for autonomous movement of a steerable surgical device that includes a first tubular element, a second tubular element longitudinally displaced from the first tubular element, and a joint comprising a flexible tubular element between the first and second tubular elements, and that is insertable into tissue of a mammalian body, the system comprising:
   a plurality of surgical device actuation elements comprising a first motor for controlling linear insertion of the steerable surgical device, a second motor for controlling rotary position of the steerable surgical device, and at least two electrically operated actuators configured to effectuate pivotal movement between the first tubular element and the second tubular element, wherein the at least two electrically operated actuators comprise shape memory alloy actuators that each extend in a longitudinal direction through longitudinal bores defined within the flexible tubular element, and wherein the shape memory alloy actuators are isolated from an exterior surface of the joint and prevented from contacting the tissue upon insertion of the steerable surgical device therein;
   an imaging apparatus comprising an ultrasound imaging probe arranged external to the mammalian body and configured to ultrasonically detect a position of a tip of the steerable surgical device within the tissue;
   at least one processor configured to:
      generate a transit path of the steerable surgical device through the tissue between an insertion point and a target point;
      control the plurality of surgical device actuation elements to advance the steerable surgical device through the tissue along at least one segment of the transit path;
      utilize signals obtained or derived from the imaging apparatus to identify the position of the tip of the steerable surgical device within the tissue, identify deviation of the position relative to the transit path, and generate an updated transit path; and
      control the plurality of surgical device actuation elements to advance the steerable surgical device through the tissue along at least one segment of the updated transit path from the position to the target point;
   wherein the system is configured to cause the steerable surgical device to transit through the tissue between the insertion point and the target point under control of the at least one processor without human intervention.

2. The system of claim 1, wherein the system further comprises at least one probe actuator configured to move the ultrasound imaging probe, wherein the at least one processor is configured to control the at least one probe actuator.

3. The system of claim 1, wherein the at least one processor is configured to generate the transit path and generate the updated transit path utilizing a Rapid-exploring Random Tree (RRT) algorithm with constraints on movement capabilities of the steerable surgical device.

4. The system of claim 1, wherein the transit path and the updated transit path each avoid one or more defined obstacles within, proximate to, or bounding the tissue.

5. The system of claim 1, wherein the transit path and the updated transit path each embody a path that minimizes damage to the tissue attributable to transit of the steerable surgical device through the tissue, while simultaneously avoiding one or more defined obstacles within, proximate to, or bounding the tissue.

6. The system of claim 1, wherein the transit path and the updated transit path each embody a path that avoids one or more defined obstacles within, proximate to, or bounding the tissue, while also exhibiting at least one of the following features (i) or (ii): (i) minimizing damage to the tissue attributable to transit of the steerable surgical device through the tissue, or (ii) minimizing distance of transit of the steerable surgical device between the insertion point and the target point.

7. The system of claim 1, wherein the steerable surgical device comprises an elongated flexible needle.

8. A method for controlling movement of a steerable surgical device that includes a first tubular element, a second tubular element longitudinally displaced from the first tubular element, and a joint comprising a flexible tubular element between the first and second tubular elements, and that is insertable into tissue of a mammalian body, the method comprising:
   generating, by at least one processor, a transit path of the steerable surgical device through the tissue extending from an insertion point to a target point, wherein the transit path avoids one or more obstacles;
   controlling, by the at least one processor, a plurality of surgical device actuation elements to advance the steerable surgical device through the tissue along at least one segment of the transit path, wherein the plurality of surgical device actuation elements comprises a first motor for controlling linear insertion of the steerable surgical device, a second motor for controlling rotary position of the steerable surgical device, and at least two electrically operated actuators configured to effectuate pivotal movement between the first tubular element and the second tubular element, wherein the at least two electrically operated actuators comprise shape memory alloy actuators that each extend in a longitudinal direction through longitudinal bores defined within the flexible tubular element, and wherein the shape memory alloy actuators are isolated from an exterior surface of the joint and prevented from contacting the tissue upon insertion of the steerable surgical device therein;

detecting, by an imaging apparatus including an ultrasound imaging probe arranged external to the mammalian body, a position of a tip of the steerable surgical device within the tissue;

identifying, by the at least one processor, position of the tip of the steerable surgical device within the tissue using signals received from the imaging apparatus;

generating, by the at least one processor, an updated transit path for controlling movement of the steerable surgical device from a current position to the target point, wherein the updated transit path avoids the one or more obstacles; and controlling, by the at least one processor, the plurality of surgical device actuation elements to advance the steerable surgical device through the tissue along at least one segment of the updated transit path;

wherein transit of the steerable surgical device through the tissue is controlled by the at least one processor without human intervention.

9. A system for autonomous movement of a steerable surgical device that includes a first tubular element, a second tubular element longitudinally displaced from the first tubular element, and a joint comprising a flexible tubular element between the first and second tubular elements, and that is insertable into tissue of a mammalian body, the system comprising:

a plurality of surgical device actuation elements comprising a first motor for controlling linear insertion of the steerable surgical device, a second motor for controlling rotary position of the steerable surgical device, and at least two electrically operated actuators configured to effectuate pivotal movement between the first tubular element and the second tubular element wherein the at least two electrically operated actuators comprise shape memory alloy actuators that each extend in a longitudinal direction through longitudinal bores defined within the flexible tubular element, and wherein the shape memory alloy actuators are isolated from an exterior surface of the joint and prevented from contacting the tissue upon insertion of the steerable surgical device therein;

an imaging apparatus comprising an ultrasound imaging probe arranged external to the mammalian body and configured to ultrasonically detect a position of a tip of the steerable surgical device within the tissue;

at least one probe actuator configured to move the ultrasound imaging probe external to the mammalian body; and at least one processor configured to:
  generate a transit path of the steerable surgical device through the tissue between an insertion point and a target point;
  control the plurality of surgical device actuation elements to advance the steerable surgical device through the tissue along at least one segment of the transit path;
  utilize signals obtained or derived from the imaging apparatus while the ultrasound imaging probe is external to the mammalian body to identify a position of the tip of the steerable surgical device within the tissue, and identify deviation of the position of the tip relative to the transit path;
  control the at least one probe actuator to cause the ultrasound imaging probe to advance substantially parallel to a segment of the transit path to a forward position ahead of the position of the tip, and control the imaging apparatus to capture multiple images of tissue planes during such movement, including at least one image of a tissue plane ahead of the position of the tip in which the tip is not visible;
  control the at least one probe actuator to cause the ultrasound imaging probe to retreat substantially parallel to the segment of the transit path to a rearward position in which the tip is detectable by the ultrasound imaging probe, and control the imaging apparatus to capture at least one image of a tissue plane in which the tip is visible;
  utilize signals obtained or derived from the imaging apparatus to generate an updated transit path; and
  control the plurality of surgical device actuation elements to advance the steerable surgical device through the tissue along at least one segment of the updated transit path from the position to the target point;

wherein the system is configured to cause the steerable surgical device to transit through the tissue between the insertion point and the target point under control of the at least one processor without human intervention.

10. The system of claim 9, wherein the at least one processor is configured to generate the transit path and generate the updated transit path utilizing a Rapid-exploring Random Tree (RRT) algorithm with constraints on movement capabilities of the steerable surgical device.

11. The system of claim 9, wherein the transit path and the updated transit path each avoid one or more defined obstacles within, proximate to, or bounding the tissue.

12. The system of claim 9, wherein the transit path and the updated transit path each embody a path that minimizes damage to the tissue attributable to transit of the steerable surgical device through the tissue, while simultaneously avoiding one or more defined obstacles within, proximate to, or bounding the tissue.

13. The system of claim 9, wherein the transit path and the updated transit path each embody a path that avoids one or more defined obstacles within, proximate to, or bounding the tissue, while also exhibiting at least one of the following features (i) or (ii): (i) minimizing damage to the tissue attributable to transit of the steerable surgical device through the tissue, or (ii) minimizing distance of transit of the steerable surgical device between the insertion point and the target point.

14. The system of claim 9, wherein the steerable surgical device comprises an elongated flexible needle.

15. The method of claim 8, wherein the generating of the transit path and the generating of the updated transit path utilize a Rapid-exploring Random Tree (RRT) algorithm with constraints on movement capabilities of the steerable surgical device.

* * * * *